US012653420B2

(12) United States Patent
Segal et al.

(10) Patent No.: US 12,653,420 B2
(45) Date of Patent: Jun. 16, 2026

(54) SYSTEM AND METHOD FOR CLASSIFYING GAIT AND POSTURE ABNORMALITY

(71) Applicant: APOS MEDICAL ASSETS LTD, Tel Aviv (IL)

(72) Inventors: Ganit Segal, Modiin-Macabim-Reut (IL); Oren Livne, Tel-Aviv (IL); Clifford Bleustein, Purchase, NY (US); Micha Breakstone, Raanana (IL)

(73) Assignee: APOS MEDICAL ASSETS LTD, Tel Aviv (IL)

( * ) Notice: Subject to any disclaimer, the term of this patent is extended or adjusted under 35 U.S.C. 154(b) by 236 days.

(21) Appl. No.: 18/265,744

(22) PCT Filed: Dec. 7, 2021

(86) PCT No.: PCT/IL2021/051457
§ 371 (c)(1),
(2) Date: Jun. 7, 2023

(87) PCT Pub. No.: WO2022/123561
PCT Pub. Date: Jun. 16, 2022

(65) Prior Publication Data
US 2024/0115159 A1     Apr. 11, 2024

Related U.S. Application Data

(60) Provisional application No. 63/155,341, filed on Mar. 2, 2021, provisional application No. 63/122,020, filed on Dec. 7, 2020.

(51) Int. Cl.
*A61B 5/103*     (2006.01)
*A61B 5/00*     (2006.01)
(Continued)

(52) U.S. Cl.
CPC .......... *A61B 5/1038* (2013.01); *A61B 5/4561* (2013.01); *A61B 5/486* (2013.01);
(Continued)

(58) Field of Classification Search
CPC ..... A61B 5/1038; A61B 5/4561; A61B 5/486; A61B 5/7267; A61B 2562/0247;
(Continued)

(56) References Cited

U.S. PATENT DOCUMENTS

| 1,021,142 A | 3/1912 | Freeman |
| 1,061,353 A | 5/1913 | Block |
| | (Continued) | |

FOREIGN PATENT DOCUMENTS

| AU | 2005262198 A1 | 1/2006 |
| CA | 2340124 A1 | 11/2000 |
| | (Continued) | |

OTHER PUBLICATIONS

Cerruto, M. A., Vedovi, E., & Mantovani, W. (2008). Women Pay Attention to Shoe Heels: Besides Causing Schizophrenia They Might Affect Your Pelvic Floor Muscle Activity !! European Urology, 53(5), 1094-1095. doi: 10.1016/j.eururo.2008.01.046.
(Continued)

*Primary Examiner* — Rex R Holmes
(74) *Attorney, Agent, or Firm* — The Roy Gross Law Firm, LLC; Roy Gross

(57)     ABSTRACT

A method comprising: receiving, with respect to each of a plurality of subjects, data comprising at least one of: (i) a data representing center of pressure (COP) of a subject during at least on gait phase; (ii) a data representing center of gravity (COG) of the subject during at least on gait phase; and; (iii) a data representing posture of the subject during at least on gait phase; processing the data to extract a plurality of features representing the data, at a training stage, training
(Continued)

a machine learning model on a training set comprising all of the plurality of features; and at an inference stage, applying the trained machine learning model to a target set of the features obtained for ma target subject, to classify posture, proprioception and/or kinesthesis of the target subject.

20 Claims, 8 Drawing Sheets

(51) Int. Cl.
| | |
|---|---|
| *G06V 10/80* | (2022.01) |
| *G06V 10/774* | (2022.01) |
| *G06V 20/40* | (2022.01) |

(52) U.S. Cl.
CPC .......... *A61B 5/7267* (2013.01); *G06V 10/811* (2022.01); *A61B 2562/0247* (2013.01); *G06V 10/774* (2022.01); *G06V 20/41* (2022.01); *G06V 2201/03* (2022.01)

(58) Field of Classification Search
CPC ..... A61B 5/112; A61B 5/4848; G06V 10/811; G06V 10/774; G06V 20/41; G06V 2201/03; G06V 40/103; G06V 40/25; G06N 3/08; G06N 20/10
See application file for complete search history.

(56) References Cited

U.S. PATENT DOCUMENTS

| | | | |
|---|---|---|---|
| 1,529,421 | A | 3/1925 | Dowdell |
| 1,736,576 | A | 11/1929 | Cable |
| 2,095,488 | A | 10/1937 | Cobb |
| 2,096,500 | A | 10/1937 | McCahan et al. |
| 2,133,302 | A | 10/1938 | Mccormick |
| 2,303,744 | A | 12/1942 | Jacobs |
| 2,311,925 | A | 2/1943 | Boos |
| 2,413,133 | A | 12/1946 | Aydelotte |
| 2,518,033 | A | 8/1950 | Lucas |
| 3,063,169 | A | 11/1962 | Cortina |
| 3,082,549 | A | 3/1963 | Dolceamore |
| 3,402,485 | A | 9/1968 | Mcmorrow |
| 3,481,332 | A | 12/1969 | Arnold |
| 3,526,976 | A | 9/1970 | Jacobs |
| 3,552,043 | A | 1/1971 | Moffa |
| 3,668,792 | A | 6/1972 | York |
| 3,782,011 | A | 1/1974 | Fisher |
| 3,797,136 | A | 3/1974 | Soleri |
| 3,805,418 | A | 4/1974 | Matuka et al. |
| 3,859,736 | A | 1/1975 | Hill et al. |
| 3,867,929 | A | 2/1975 | Joyner et al. |
| 3,916,538 | A | 11/1975 | Loseff |
| 3,940,128 | A | 2/1976 | Ragone |
| 4,030,213 | A | 6/1977 | Daswick |
| 4,071,963 | A | 2/1978 | Fukuoka |
| 4,109,661 | A | 8/1978 | Fukuoka |
| 4,176,459 | A | 12/1979 | Perser et al. |
| 4,241,523 | A | 12/1980 | Daswick |
| 4,262,434 | A | 4/1981 | Michelotti |
| 4,348,821 | A | 9/1982 | Daswick |
| RE31,173 | E | 3/1983 | Daswick |
| 4,378,643 | A | 4/1983 | Johnson |
| 4,577,417 | A | 3/1986 | Cole |
| 4,586,706 | A | 5/1986 | Chen |
| 4,629,181 | A | 12/1986 | Krive |
| 4,653,748 | A | 3/1987 | Seel et al. |
| 4,660,548 | A | 4/1987 | Bucher |
| 4,660,826 | A | 4/1987 | Lee |
| 4,670,996 | A | 6/1987 | Dill |
| 4,739,986 | A | 4/1988 | Kucharik et al. |
| 4,805,320 | A | 2/1989 | Goldenberg et al. |
| 4,821,432 | A | 4/1989 | Reiber |
| 4,841,648 | A | 6/1989 | Shaffer et al. |
| 4,892,090 | A | 1/1990 | Kaeser |
| 4,907,355 | A | 3/1990 | Allen et al. |
| 4,984,377 | A | 1/1991 | Schneider |
| 5,014,706 | A | 5/1991 | Philipp |
| 5,018,511 | A | 5/1991 | Yokoi |
| 5,035,418 | A | 7/1991 | Harabayashi |
| 5,103,806 | A | 4/1992 | McLeod et al. |
| 5,113,850 | A | 5/1992 | Larremore et al. |
| 5,170,776 | A | 12/1992 | Pecheux |
| 5,188,578 | A | 2/1993 | Voigt |
| 5,203,321 | A | 4/1993 | Donovan et al. |
| 5,211,160 | A | 5/1993 | Talish et al. |
| 5,243,775 | A | 9/1993 | Swain |
| 5,251,508 | A | 10/1993 | Robbins |
| 5,337,494 | A | 8/1994 | Ricker |
| 5,400,528 | A | 3/1995 | Skinner et al. |
| D357,347 | S | 4/1995 | Leick |
| 5,518,476 | A | 5/1996 | McLeon |
| 5,520,612 | A | 5/1996 | Winder et al. |
| 5,524,365 | A | 6/1996 | Goldenberg |
| 5,533,282 | A | 7/1996 | Kataoka et al. |
| 5,549,527 | A | 8/1996 | Yu |
| 5,584,787 | A | 12/1996 | Guidry |
| 5,603,334 | A | 2/1997 | Sharp |
| 5,643,145 | A | 7/1997 | Lo et al. |
| 5,643,164 | A | 7/1997 | Teff |
| 5,647,145 | A | 7/1997 | Russell et al. |
| 5,682,690 | A | 11/1997 | Chang |
| 5,685,807 | A | 11/1997 | Tong et al. |
| 5,730,705 | A | 3/1998 | Talish et al. |
| D394,343 | S | 5/1998 | Marshall et al. |
| D394,541 | S | 5/1998 | Burgess |
| 5,848,954 | A | 12/1998 | Stearns et al. |
| 5,860,228 | A | 1/1999 | Bathum |
| 5,887,360 | A | 3/1999 | Bucalo et al. |
| 5,897,464 | A | 4/1999 | Mcleod |
| 5,902,214 | A | 5/1999 | Makikawa et al. |
| D412,393 | S | 8/1999 | Aquino |
| 5,960,568 | A | 10/1999 | Bell et al. |
| D416,672 | S | 11/1999 | Curley, Jr. et al. |
| 6,019,712 | A | 2/2000 | Duncan |
| 6,035,559 | A | 3/2000 | Freed et al. |
| 6,063,046 | A | 5/2000 | Allum |
| 6,102,832 | A | 8/2000 | Tani |
| 6,108,944 | A | 8/2000 | Savoie |
| 6,115,943 | A | 9/2000 | Gyr |
| 6,126,577 | A | 10/2000 | Chang |
| 6,170,173 | B1 | 1/2001 | Caston |
| 6,176,817 | B1 | 1/2001 | Carey et al. |
| D439,733 | S | 4/2001 | Savoie |
| 6,277,057 | B1 | 8/2001 | Hayden |
| 6,283,897 | B1 | 9/2001 | Patton |
| D448,920 | S | 10/2001 | Montross et al. |
| 6,311,416 | B1 | 11/2001 | Cohen |
| 6,315,786 | B1 | 11/2001 | Smuckler |
| 6,349,487 | B1 | 2/2002 | Hice |
| 6,389,712 | B1 | 5/2002 | Schelling |
| 6,389,714 | B1 | 5/2002 | Mack |
| 6,393,735 | B1 | 5/2002 | Berggren |
| 6,432,070 | B1 | 8/2002 | Talish et al. |
| 6,464,654 | B1 | 10/2002 | Montgomery et al. |
| 6,494,117 | B1 | 12/2002 | Bryne |
| 6,505,420 | B1 | 1/2003 | Litchfield et al. |
| 6,511,404 | B2 | 1/2003 | Tu |
| 6,519,873 | B1 | 2/2003 | Buttigieg |
| 6,551,225 | B1 | 4/2003 | Romero |
| 6,557,272 | B2 | 5/2003 | Pavone |
| 6,652,432 | B2 | 11/2003 | Smith |
| D482,851 | S | 12/2003 | McClaskie |
| 6,692,419 | B2 | 2/2004 | Chen |
| D488,915 | S | 4/2004 | Girbaud et al. |
| D488,920 | S | 4/2004 | Izen et al. |
| 6,742,289 | B2 | 6/2004 | Celmo |
| 6,785,987 | B2 | 9/2004 | Bucalo et al. |
| 6,792,703 | B2 | 9/2004 | Cohen |
| 6,793,609 | B1 | 9/2004 | Fan |
| 6,796,056 | B2 | 9/2004 | Swigart |
| 6,811,523 | B1 | 11/2004 | Timmer |
| 6,880,267 | B2 | 4/2005 | Smaldone et al. |

(56) References Cited

U.S. PATENT DOCUMENTS

| | | | |
|---|---|---|---|
| 6,979,287 B2 | 12/2005 | Elbaz et al. | |
| 7,004,895 B2 | 2/2006 | Perry et al. | |
| 7,081,070 B1 | 7/2006 | Washington et al. | |
| 7,101,330 B2 | 9/2006 | Elbaz et al. | |
| 7,165,343 B2 | 1/2007 | Fukui | |
| 7,266,912 B2 | 9/2007 | Whatley | |
| 7,287,340 B2 | 10/2007 | Talbott | |
| 7,373,740 B2 | 5/2008 | Lo | |
| 7,462,158 B2 | 12/2008 | Mor | |
| 7,500,324 B1 | 3/2009 | Power et al. | |
| 7,621,057 B1 | 11/2009 | Julian et al. | |
| 7,707,751 B2 | 5/2010 | Avent et al. | |
| 7,984,569 B2 | 7/2011 | Chaney et al. | |
| 8,038,583 B2 | 10/2011 | Bailar | |
| D648,517 S | 11/2011 | Vestuti et al. | |
| 8,079,159 B1 | 12/2011 | Rosa | |
| 8,205,356 B2 | 6/2012 | Ellis | |
| 8,424,221 B2 | 4/2013 | Litchfield et al. | |
| 8,453,354 B2 | 6/2013 | Baker | |
| 8,533,980 B2 | 9/2013 | Elbaz et al. | |
| 8,713,817 B2 | 5/2014 | Litchfield et al. | |
| 8,740,757 B1 | 6/2014 | FioRito et al. | |
| 8,758,207 B2 | 6/2014 | Elbaz et al. | |
| 8,959,798 B2 | 2/2015 | Pfister | |
| 8,984,770 B1 | 3/2015 | Piontkowski | |
| 9,055,788 B2 | 6/2015 | Elbaz et al. | |
| 9,271,895 B2 | 3/2016 | Mor et al. | |
| 9,357,812 B2 | 6/2016 | Elbaz et al. | |
| 9,445,965 B2 | 9/2016 | Mor et al. | |
| 9,693,927 B2 | 7/2017 | Mor et al. | |
| 9,788,597 B2 | 10/2017 | Elbaz et al. | |
| 9,861,509 B2 | 1/2018 | Elbaz et al. | |
| 9,968,159 B2 | 5/2018 | Morrison et al. | |
| 10,010,743 B2 | 7/2018 | Elbaz et al. | |
| 10,182,609 B2 | 1/2019 | Bryne | |
| 10,632,006 B2 | 4/2020 | Elbaz et al. | |
| 10,744,368 B2 | 8/2020 | Elbaz et al. | |
| 10,750,812 B2 | 8/2020 | Mor et al. | |
| 11,219,574 B2 | 1/2022 | Depta | |
| 11,363,852 B2 | 6/2022 | Mor et al. | |
| 11,504,571 B2 | 11/2022 | Elbaz et al. | |
| 11,589,646 B1 | 2/2023 | Weschler | |
| 2001/0011427 A1 | 8/2001 | Seydel et al. | |
| 2002/0026730 A1 | 3/2002 | Whatley | |
| 2002/0038522 A1 | 4/2002 | Houser et al. | |
| 2002/0092201 A1 | 7/2002 | Kraeuter et al. | |
| 2002/0100190 A1 | 8/2002 | Pellerin | |
| 2002/0139011 A1 | 10/2002 | Kerrigan | |
| 2002/0166258 A1 | 11/2002 | Posa | |
| 2003/0056394 A1 | 3/2003 | Yu | |
| 2003/0093925 A1 | 5/2003 | Auger et al. | |
| 2003/0140523 A1 | 7/2003 | Issler | |
| 2003/0148865 A1 | 8/2003 | Handshoe | |
| 2003/0153849 A1 | 8/2003 | Huckle et al. | |
| 2003/0188458 A1 | 10/2003 | Kelly | |
| 2004/0033864 A1 | 2/2004 | Elbaz et al. | |
| 2004/0033874 A1 | 2/2004 | Elbaz et al. | |
| 2004/0053751 A1 | 3/2004 | Pizolato | |
| 2004/0079001 A1 | 4/2004 | McMullin | |
| 2004/0082886 A1 | 4/2004 | Timpson | |
| 2004/0111925 A1 | 6/2004 | Fukui | |
| 2004/0181969 A1 | 9/2004 | Smaldone et al. | |
| 2005/0022425 A1 | 2/2005 | Brown | |
| 2005/0032965 A1 | 2/2005 | Valero | |
| 2005/0124740 A1 | 6/2005 | Klockmann et al. | |
| 2005/0235526 A1 | 10/2005 | Kim | |
| 2005/0246924 A1 | 11/2005 | Masoodifar | |
| 2006/0021260 A1 | 2/2006 | Kim | |
| 2006/0042119 A1 | 3/2006 | Workman et al. | |
| 2006/0090372 A1 | 5/2006 | Kim | |
| 2006/0130372 A1 | 6/2006 | Auger et al. | |
| 2006/0196087 A1 | 9/2006 | Sellers et al. | |
| 2006/0241224 A1 | 10/2006 | Krafczyk et al. | |
| 2007/0051020 A1 | 3/2007 | Tajima et al. | |
| 2007/0079532 A1 | 4/2007 | Ramirez | |
| 2007/0193071 A1 | 8/2007 | Gilmore | |
| 2007/0209239 A1 | 9/2007 | Kelly | |
| 2007/0271816 A1 | 11/2007 | Workman et al. | |
| 2007/0289170 A1 | 12/2007 | Avent et al. | |
| 2008/0010586 A1 | 1/2008 | Betancourt et al. | |
| 2008/0134541 A1 | 6/2008 | Bar-Haim et al. | |
| 2008/0229611 A1 | 9/2008 | Chiodo et al. | |
| 2008/0242518 A1 | 10/2008 | Elbaz et al. | |
| 2008/0263898 A1 | 10/2008 | Gueh | |
| 2009/0113760 A1 | 5/2009 | Dominguez | |
| 2009/0172975 A1 | 7/2009 | Keough | |
| 2009/0193687 A1 | 8/2009 | Kim | |
| 2009/0199429 A1 | 8/2009 | Ellis | |
| 2009/0215952 A1 | 8/2009 | Guy et al. | |
| 2010/0050476 A1 | 3/2010 | Elbaz et al. | |
| 2010/0186262 A1 | 7/2010 | Krikorian et al. | |
| 2010/0236094 A1 | 9/2010 | Ryu | |
| 2010/0236095 A1 | 9/2010 | Reed | |
| 2010/0251565 A1 | 10/2010 | Litchfield et al. | |
| 2010/0251567 A1 | 10/2010 | Mcinnis et al. | |
| 2010/0281710 A1 | 11/2010 | Killion | |
| 2010/0281716 A1 | 11/2010 | Luthi et al. | |
| 2010/0325919 A1 | 12/2010 | Elbaz et al. | |
| 2011/0009982 A1 | 1/2011 | King et al. | |
| 2011/0047831 A1 | 3/2011 | Elbaz et al. | |
| 2011/0072684 A1 | 3/2011 | Stubblefield | |
| 2011/0123099 A1 | 5/2011 | Pfeiffer et al. | |
| 2011/0126422 A1 | 6/2011 | Vattes et al. | |
| 2012/0073166 A1 | 3/2012 | Bryla | |
| 2012/0227288 A1 | 9/2012 | Teteriatnikov | |
| 2013/0055597 A1 | 3/2013 | Hennig | |
| 2013/0116726 A1 | 5/2013 | Mor et al. | |
| 2013/0165834 A1 | 6/2013 | Elbaz et al. | |
| 2013/0185955 A1 | 7/2013 | Cheng | |
| 2013/0196829 A1 | 8/2013 | Elbaz et al. | |
| 2013/0199054 A1 | 8/2013 | Litchfield et al. | |
| 2014/0109444 A1 | 4/2014 | Dumont | |
| 2014/0149072 A1 | 5/2014 | Rutschmann | |
| 2014/0309692 A1 | 10/2014 | Mor et al. | |
| 2014/0317959 A1 | 10/2014 | Elbaz et al. | |
| 2014/0325769 A1 | 11/2014 | Elbaz et al. | |
| 2015/0119767 A1 | 4/2015 | Mor et al. | |
| 2015/0150713 A1 | 6/2015 | Ward | |
| 2015/0165690 A1 | 6/2015 | Tow | |
| 2016/0147959 A1 | 5/2016 | Mariottini et al. | |
| 2016/0278473 A1 | 9/2016 | Elbaz et al. | |
| 2017/0066196 A1 | 3/2017 | Beard et al. | |
| 2017/0068774 A1 | 3/2017 | Cluckers et al. | |
| 2017/0105476 A1 | 4/2017 | Morrison et al. | |
| 2018/0085055 A1* | 3/2018 | Annoni | A61B 5/4824 |
| 2018/0168279 A1 | 6/2018 | Mor et al. | |
| 2018/0168841 A1 | 6/2018 | Elbaz et al. | |
| 2018/0178067 A1 | 6/2018 | Rousian | |
| 2018/0220737 A1 | 8/2018 | Piontkowski et al. | |
| 2018/0279915 A1* | 10/2018 | Huang | A61B 5/6807 |
| 2018/0368503 A1 | 12/2018 | Cook et al. | |
| 2019/0009127 A1 | 1/2019 | Elbaz et al. | |
| 2019/0053567 A1 | 2/2019 | Thomas | |
| 2019/0069630 A1 | 3/2019 | Hopkins | |
| 2019/0110918 A1 | 4/2019 | Darby, II et al. | |
| 2019/0275403 A1 | 9/2019 | Rudan | |
| 2020/0011658 A1 | 1/2020 | Chuyko et al. | |
| 2020/0093675 A1 | 3/2020 | Hale | |
| 2020/0230014 A1 | 7/2020 | Kim | |
| 2020/0359737 A1 | 11/2020 | Sung | |
| 2020/0375302 A1 | 12/2020 | Mor et al. | |
| 2020/0375501 A1 | 12/2020 | Motamedi et al. | |
| 2020/0376323 A1 | 12/2020 | Elbaz et al. | |
| 2022/0022595 A1 | 1/2022 | Girard et al. | |
| 2022/0039515 A1 | 2/2022 | Livne et al. | |
| 2022/0248799 A1 | 8/2022 | Mor et al. | |
| 2022/0361628 A1 | 11/2022 | Natanson et al. | |
| 2023/0000396 A1* | 1/2023 | Coffey | A61B 5/1117 |
| 2023/0029846 A1 | 2/2023 | Livne et al. | |

(56) References Cited

U.S. PATENT DOCUMENTS

| | | | |
|---|---|---|---|
| 2023/0140074 A1 | 5/2023 | Bernhard |
| 2023/0232934 A1 | 7/2023 | Lightheart |

FOREIGN PATENT DOCUMENTS

| | | |
|---|---|---|
| CN | 101279636 A | 10/2008 |
| CN | 101836778 B | 5/2013 |
| CN | 109662384 A | 4/2019 |
| CN | 108741393 B | 6/2021 |
| CN | 113453576 A | 9/2021 |
| CZ | 2016457 A3 | 2/2018 |
| DE | 1907894 U | 1/1965 |
| DE | 29701013 U1 | 3/1997 |
| DE | 29902731 U1 | 3/2000 |
| DE | 10133863 A1 | 2/2003 |
| EP | 0925809 A1 | 6/1999 |
| EP | 0630926 B1 | 12/1999 |
| EP | 1038459 A1 | 9/2000 |
| EP | 2462827 A2 | 6/2012 |
| EP | 2787853 A1 | 10/2014 |
| EP | 2787853 B1 | 10/2021 |
| FR | 1128009 A | 1/1957 |
| FR | 2820329 A1 | 8/2002 |
| JP | S4931233 B1 | 8/1974 |
| JP | S61119282 A | 6/1986 |
| JP | H08763 A | 1/1996 |
| JP | H09308706 A | 12/1997 |
| JP | H114842 A | 1/1999 |
| JP | 2000084035 A | 3/2000 |
| JP | 2005081030 A | 3/2005 |
| JP | 2005287726 A | 10/2005 |
| JP | 2005536247 A | 12/2005 |
| JP | 2006055600 A | 3/2006 |
| JP | 2006247197 A | 9/2006 |
| JP | 2007029700 A | 2/2007 |
| JP | 2007330469 A | 12/2007 |
| JP | 2008264023 A | 11/2008 |
| JP | 2009018124 A | 1/2009 |
| JP | 2010115291 A | 5/2010 |
| JP | 2013534446 A | 9/2013 |
| JP | 2016501114 A | 1/2016 |
| KR | 20030058556 A | 7/2003 |
| KR | 20050039686 A | 4/2005 |
| KR | 20150001713 A | 1/2015 |
| KR | 20190107155 A | 9/2019 |
| NL | 8502659 A | 4/1987 |
| RU | 2033132 C1 | 4/1995 |
| RU | 2343946 C2 | 1/2009 |
| WO | 1996020651 A1 | 7/1996 |
| WO | 1997013422 A1 | 4/1997 |
| WO | 1998031245 A1 | 7/1998 |
| WO | 2000067846 A1 | 11/2000 |
| WO | 2001037693 A1 | 5/2001 |
| WO | 2001077693 A1 | 10/2001 |
| WO | 2002037995 A1 | 5/2002 |
| WO | 2003090868 A1 | 11/2003 |
| WO | 2004016321 A2 | 2/2004 |
| WO | 2004043185 A1 | 5/2004 |
| WO | 2005107868 A1 | 11/2005 |
| WO | 2006005139 A1 | 1/2006 |
| WO | 2006065070 A1 | 6/2006 |
| WO | 2010025120 A2 | 3/2010 |
| WO | 2011024162 A1 | 3/2011 |
| WO | 2012001678 A2 | 1/2012 |
| WO | 2012001685 A1 | 1/2012 |
| WO | 2012011109 A2 | 1/2012 |
| WO | 2013084212 A1 | 6/2013 |
| WO | 2013084213 A1 | 6/2013 |
| WO | 2016199150 A1 | 12/2016 |
| WO | 2020086792 A1 | 4/2020 |
| WO | 2020121314 A1 | 6/2020 |

OTHER PUBLICATIONS

Julia-Guilloteau V, Denys P, Bernabé J, Mevel K, Chartier-Kastler E, Alexandre L, Giuliano F. Urethral closure. Mechanisms during sneezing-induced stress in anesthetized female cats. Am J Physiol Regul Integr Comp Physiol. Sep. 2007;293(3):R1357-67. doi: 10.1152/ajpregu.00003.2007. Epub Jul. 11, 2007. PMID: 17626129.

Merriam-Webster. (n.d.). Resilience. In Merriam-Webster.com dictionary. Retrieved Nov. 13, 2022, from https://www.merriam-webster.com/dictionary/resilience.

Nieuwenhuijzen, P. H. J. A., Grüneberg, C., & Duysens, J. (2002). Mechanically induced ankle inversion during human walking and jumping. Journal of neuroscience methods, 117(2), 133-140.

Suny Upstate Health Science Center at Syracuse. https://web.archive.org/web/20090826045741/http://www.upstate.edu/cdb/grossanat/limbs6.shtml (2013).

Nakamura S. et al. An analysis of soft tissue loading in the foot—a preliminary report. Bull Prosthet Res. 1981 Spring; 10-35:27-34., https://www.rehab.research.va.gov/jour/81/18/1/pdf/nakamura.pdf).

Toussaint, Godfried T. (1983). "Solving geometric problems with the rotating calipers". Proc. MELECON '83, Athens.

Nedic, A. 2008. Optimization I. Lecture Notes. Network Mathematics Graduate Programme Hamilton Institute, Maynooth, Ireland. Delivered Aug. 4, 2008.

Mansour, J.M. (2013). Biomechanics of cartilage.

Bennett LD, Buckland-Wright JC. Meniscal and articular cartilage changes in knee osteoarthritis: a cross-sectional double-contrast macroradiographic study. Rheumatology (Oxford). Aug. 2002;41(8):917-23. doi: 10.1093/rheumatology/41.8.917. PMID: 12154209.

Neogi T, Felson D, Niu J, Nevitt M, Lewis CE, Aliabadi P, Sack B, Torner J, Bradley L, Zhang Y. Association between radiographic features of knee osteoarthritis and pain: results from two cohort studies. BMJ. Aug. 2, 20091;339:b2844. doi: 10.1136/bmj.b2844. PMID: 19700505; PMCID: PMC2730438.

Hunter DJ, Gerstenfeld L, Bishop G, Davis AD, Mason ZD, Einhorn TA, Maciewicz RA, Newham P, Foster M, Jackson S, Morgan EF. Bone marrow lesions from osteoarthritis knees are characterized by sclerotic bone that is less well mineralized. Arthritis Res Ther. 2009;11(1):R11. doi: 10.1186/ar2601. Epub Jan. 26, 2009. PMID: 19171047; PMCID: PMC2688243.

Beattie KA, Duryea J, Pui M, O'Neill J, Boulos P, Webber CE, Eckstein F, Adachi JD. Minimum joint space width and tibial cartilage morphology in the knees of healthy individuals: a cross-sectional study. BMC Musculoskelet Disord. Sep. 8, 2008;9:119. doi: 10.1186/1471-2474-9-119. PMID: 18778479; PMCID: PMC2542509.

Pavelká K, Gatterová J, Olejarová M, Machacek S, Giacovelli G, Rovati LC. Glucosamine sulfate use and delay of progression of knee osteoarthritis: a 3-year, randomized, placebo-controlled, double-blind study. Arch Intern Med. Oct. 14, 2002;162(18):2113-23. doi: 10.1001/archinte.162.18.2113. PMID: 12374520.

Apos®. (Nov. 20, 2013). Apos®—How it Works [Video]. YouTube. Retrieved Dec. 15, 2022, from https://www.youtube.com/watch?v=mjqloxr9bYU.

M.A. Cerruto, E. Vedovi, S. Dalla Riva, S. Rossi, S. Cardarelli, p. Curi, et al. The Effect of Ankle Inclination in Upright Position On the Electromyigraphic Activity of Pelvic Floor Muscles in Women With Stress Urinary Incontinence. European Urology Supplements. vol. 6 Issue 2 p. 102. Mar. 2007.

M. Khajehei and F. Etemady, "Data Mining and Medical Research Studies," 2010 Second International Conference on Computational Intelligence, Modelling and Simulation, 2010, pp. 119-122, doi: 10.1109/CIMSiM.2010.24.

Anguera de Sojo, A., Barreiro, J.M., Lara, J., Lizcano, D. (2016). Applying data mining techniques to medical time series: An empirical case study in electroencephalography and stabilometry. Computational and Structural Biotechnology Journal. 14. 10.1016/j.csbj.2016.05.002.

(56)         References Cited

OTHER PUBLICATIONS

Tanaka, K., Ujihashi, S., Iwasaki, M., & Inou, N. (2000). Correlations between the Mechanical Properties of Running Shoes and Sensory Evaluations of Distance Runners in Relation to Hardness of Tracks. Japan Society of Sports Industry. vol 10. No 1. 35-43 DOI: 10.5997/sposun.10.35.

Hsu AL, Tang PF, Jan MH. Analysis of impairments influencing gait velocity and asymmetry of hemiplegic patients after mild to moderate stroke. Arch Phys Med Rehabil. Aug. 2003;84(8):1185-93. doi: 10.1016/s0003-9993(03)00030-3. PMID: 12917858.

Detrembleur C, van den Hecke A, Dierick F. Motion of the body centre of gravity as a summary indicator of the mechanics of human pathological gait. Gait Posture. Dec. 2000; 12(3):243-50. doi: 10.1016/s0966-6362(00)00081-3. PMID: 11154935.

Whittle, M.W. (1996). Clinical gait analysis: A review. Human Movement Science, 15, 369-387.

Hausdorff JM. Gait variability: methods, modeling and meaning. J Neuroeng Rehabil. Jul. 20, 2005;2:19. doi: 10.1186/1743-0003-2-19. PMID: 16033650; Pmcid: PMC1185560.

Dierick F, Domicent C, Detrembleur C. Relationship between antagonistic leg muscles co-contractions and body centre of gravity mechanics in different level gait disorders. J Electromyogr Kinesiol. Feb. 2002; 12(1):59-66. doi: 10.1016/s1050-6411(01)00034-7. PMID: 11804812.

Horak, F. B. (1997). Clinical assessment of balance disorders. Gait & posture, 6(1), 76-84.

Klebe S, Stolze H, Kopper F, Lorenz D, Wenzelburger R, Volkmann J, Porschke H, Deuschl G. Gait analysis of sporadic and hereditary spastic paraplegia. J Neurol. May 2004;251(5):571-8. doi: 10.1007/s00415-004-0366-7. PMID:15164190.

Ackermann, M., & Schiehlen, W. (2006). Dynamic analysis of human gait disorder and metabolical cost estimation. Archive of Applied Mechanics, 75(10), 569-594.

Sinaki M, Brey RH, Hughes CA, Larson DR, Kaufman KR. Balance disorder and increased risk of falls in osteoporosis and kyphosis: significance of kyphotic posture and muscle strength. Osteoporos Int. Aug. 2005; 16(8): 1004-10. doi: 10.1007/s00198-004-1791-2. Epub Nov. 12, 2004. PMID: 15549266.

Dietz V. Proprioception and locomotor disorders. Nat Rev Neurosci. Oct. 2002; 3(10):781-90. doi: 10.1038/nrn939. PMID: 12360322.

Kamegaya M, Shinohara Y. Gait disorders and leg deformities in children. J Orthop Sci. 2002;7(1):154-9. doi: 10.1007/s776-002-8439-9. PMID: 11819150.

Molloy M, McDowell BC, Kerr C, Cosgrove AP. Further evidence of validity of the Gait Deviation Index. Gait Posture. Apr. 2010;31(4):479-82. doi: 10.1016/j.gaitpost.2010.01.025. Epub Mar. 11, 2010. PMID: 20226675.

Sudarsky L. Psychogenic gait disorders. Semin Neurol. Jul. 2006;26(3):351-6. doi: 10.1055/s-2006-945523. PMID: 16791781.

Woollacott MH. Systems contributing to balance disorders in older adults. J Gerontol A Biol Sci Med Sci. Aug. 2000;55 (8):M424-8. doi: 10.1093/gerona/55.8.m424. PMID: 10952363.

Rubino FA. Gait disorders. Neurologist. Jul. 2002;8(4):254-62. doi: 10.1097/00127893-200207000-00005. PMID: 12803684.

Thomson AP, Sills JA. Diagnosis of functional illness presenting with gait disorder. Arch Dis Child. Feb. 1988;63 (2): 148-53. doi: 10.1136/adc.63.2.148. PMID: 3348662; PMCID: PMC1778753.

Alexander NB, Goldberg A. Gait disorders: search for multiple causes. Cleve Clin J Med. Jul. 2005;72(7):586, 589-90, 592-4 passim. doi: 10.3949/ccjm.72.7.586. PMID: 16044655.

Meyer, D., Denzler, J., & Niemann, H. (Oct. 1997). Model based extraction of articulated objects in image sequences for gait analysis. In Proceedings of International Conference on Image Processing (vol. 3, pp. 78-81). IEEE.

Haim A, Rozen N, Dekel S, Halperin N, Wolf A. Control of knee coronal plane moment via modulation of center of pressure: a prospective gait analysis study. J Biomech. Oct. 20, 2008;41(14):3010-6. doi: 10.1016/j.jbiomech.2008.07.029. Epub Sep. 20, 2008. PMID: 18805527.

Haim A, Rozen N, Wolf A. The influence of sagittal center of pressure offset on gait kinematics and kinetics. J Biomech. Mar. 22, 2010;43(5):969-77. doi: 10.1016/j.jbiomech.2009.10.045. Epub Jan. 4, 2010. PMID: 20047747.

Haim A, Wolf A, Rubin G, Genis Y, Khoury M, Rozen N. Effect of center of pressure modulation on knee adduction moment in medial compartment knee osteoarthritis. J Orthop Res. Nov. 2011;29(11): 1668-74. doi: 10.1002/jor.21422. Epub Apr. 13, 2011. PMID: 21491477.

Debbi EM, Wolf A, Haim A. Detecting and quantifying global instability during a dynamic task using kinetic and kinematic gait parameters. J Biomech. May 11, 2012;45(8): 1366-71. doi: 10.1016/j.jbiomech.2012.03.007. Epub Apr. 11, 2012. PMID: 22498314.

Khoury M, Wolf A, Debbi EM, Herman A, Haim A. Foot center of pressure trajectory alteration by biomechanical manipulation of shoe design. Foot Ankle Int. Apr. 2013;34(4):593-8. doi: 10.1177/1071100713477613. Epub Feb. 28, 2013. PMID: 23449662.

Solomonow-Avnon D, Wolf A, Herman A, Rozen N, Haim A. Reduction of frontal-plane hip joint reaction force via medio-lateral foot center of pressure manipulation: a pilot study. J Orthop Res. Feb. 2015;33(2):261-9. doi: 10.1002/ jor.22744. Epub Sep. 25, 2014. PMID: 25256253.

Khoury M, Haim A, Herman A, Rozen N, Wolf A. Alteration of the foot center of pressure trajectory by an unstable shoe design. J Foot Ankle Res. Dec. 1, 2015;8:67. doi: 10.1186/s13047-015-0124-3. PMID: 26628923; PMCID: PMC4666148.

Solomonow-Avnon D, Haim A, Levin D, Elboim-Gabyzon M, Rozen N, Peled E, Wolf A. Reduction of hip joint reaction force via medio-lateral foot center of pressure manipulation in bilateral hip osteoarthritis patients. J Orthop Res. Oct. 2016;34(10): 1762-1771. doi: 10.1002/jor.23190. Epub Feb. 29, 2016. PMID: 26865531.

Solomonow-Avnon D, Herman A, Wolf A. Mechanism of reducing knee adduction moment by shortening of the knee lever arm via medio-lateral manipulation of foot center of pressure: A pilot study. J Biomech. Jan. 23, 2019;83:143-149. doi: 10.1016/j.jbiomech.2018. 11.041. Epub Nov. 29, 2018. PMID: 30527391.

Shaulian H, Solomonow-Avnon D, Herman A, Rozen N, Haim A, Wolf A. The effect of center of pressure alteration on the ground reaction force during gait: A statistical model. Gait Posture. Oct. 2018; 66:107-113. doi: 10.1016/j. gaitpost.2018.08.013. Epub Aug. 17, 2018. PMID: 30172216.

Solomonow-Avnon D, Herman A, Giwnewer U, Rozen N, Elbaz A, Mor A, Wolf A. Trunk kinematic, kinetic, and neuro-muscular response to foot center of pressure translation along the medio-lateral foot axis during gait. J Biomech. Mar. 27, 2019;86:141-148. doi: 10.1016/j.jbiomech.2019.01.052. Epub Feb. 12, 2019. PMID: 30777339.

Khoury-Mireb M, Solomonow-Avnon D, Rozen N, Wolf A. The effect of unstable shoe designs on the variability of gait measures. Gait Posture. Mar. 2019; 69:60-65. doi: 10.1016/j.gaitpost.2019.01. 017. Epub Jan. 14, 2019. PMID: 30677708.

Goryachev Y, Debbi EM, Haim A, Wolf A. The effect of manipulation of the center of pressure of the foot during gait on the activation patterns of the lower limb musculature. J Electromyogr Kinesiol. Apr. 2011;21(2):333-9. doi: 10.1016/j.jelekin.2010.11. 009. Epub Jan. 6, 2011. PMID: 21215655.

Goryachev Y, Debbi EM, Haim A, Rozen N, Wolf A. Foot center of pressure manipulation and gait therapy influence lower limb muscle activation in patients with osteoarthritis of the knee. J Electromyogr Kinesiol. Oct. 2011;21(5):704-11. doi: 10.1016/j.jelekin.2011.05. 001. PMID: 21684760.

Solomonow-Avnon D, Levin D, Elboim-Gabyzon M, Rozen N, Peled E, Wolf A. Neuromuscular response of hip-spanning and low back muscles to medio-lateral foot center of pressure manipulation during gait. J Electromyogr Kinesiol. Jun. 2016;28:53-60. doi: 10.1016/j.jelekin.2016.02.010. Epub Mar. 9, 2016. PMID: 27016625.

Massion J. Postural control system. Curr Opin Neurobiol. Dec. 1994;4(6):877-87. doi: 10.1016/0959-4388(94)90137-6. PMID: 7888772.

PCT International Search Report for International Application No. PCT/IL2021/051457, mailed Mar. 14, 2022, 3pp.

PCT Written Opinion for International Application No. PCT/IL2021/051457, mailed Mar. 14, 2022, 5pp.

(56)         References Cited

OTHER PUBLICATIONS

PCT International Preliminary Report on Patentability for International Application No. PCT/IL2021/051457, issued Jun. 13, 2023, 6p.

* cited by examiner

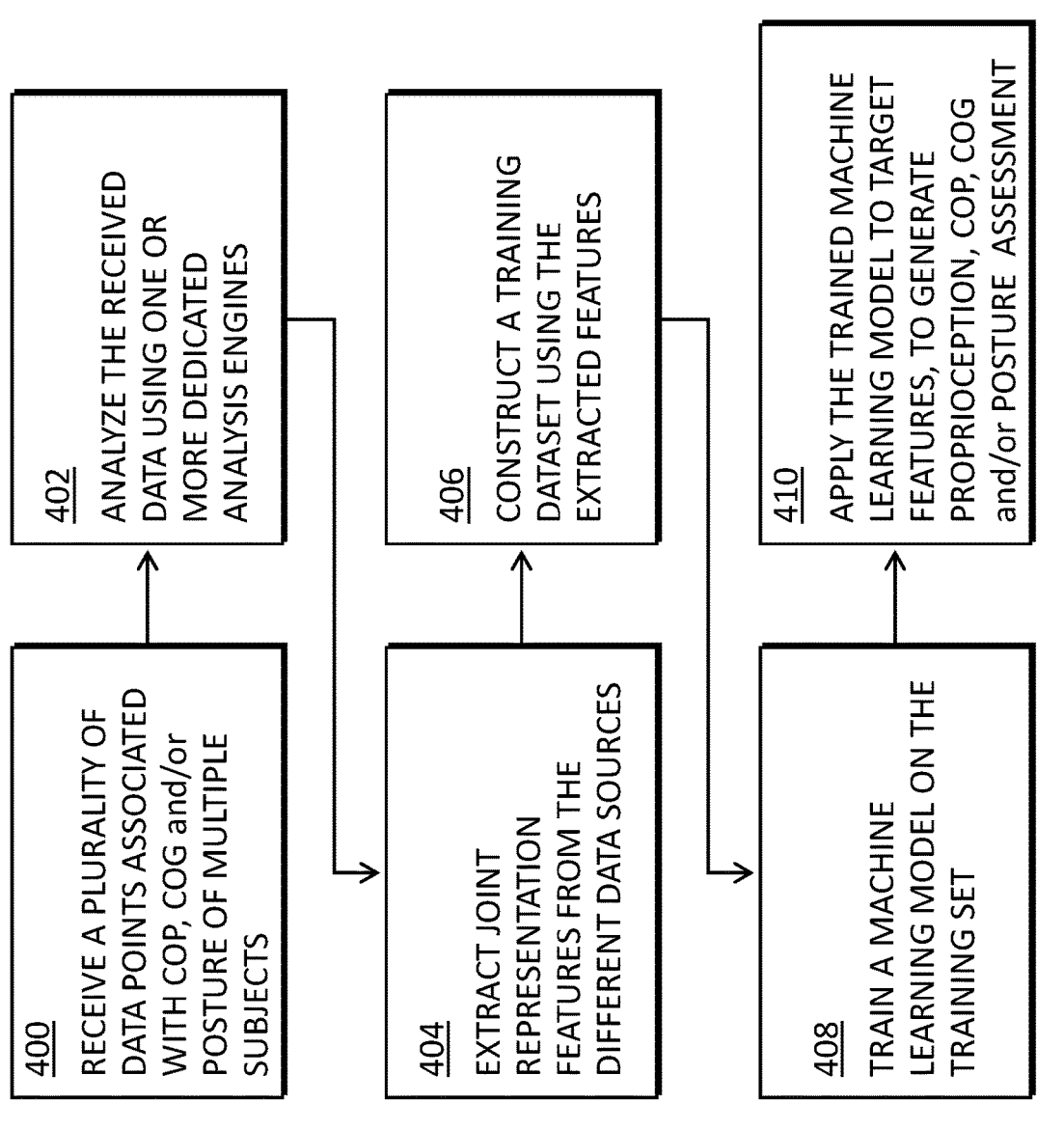

400
RECEIVE A PLURALITY OF DATA POINTS ASSOCIATED WITH COP, COG and/or POSTURE OF MULTIPLE SUBJECTS

402
ANALYZE THE RECEIVED DATA USING ONE OR MORE DEDICATED ANALYSIS ENGINES

404
EXTRACT JOINT REPRESENTATION FEATURES FROM THE DIFFERENT DATA SOURCES

406
CONSTRUCT A TRAINING DATASET USING THE EXTRACTED FEATURES

408
TRAIN A MACHINE LEARNING MODEL ON THE TRAINING SET

410
APPLY THE TRAINED MACHINE LEARNING MODEL TO TARGET FEATURES, TO GENERATE PROPRIOCEPTION, COP, COG and/or POSTURE ASSESSMENT

FIG. 4

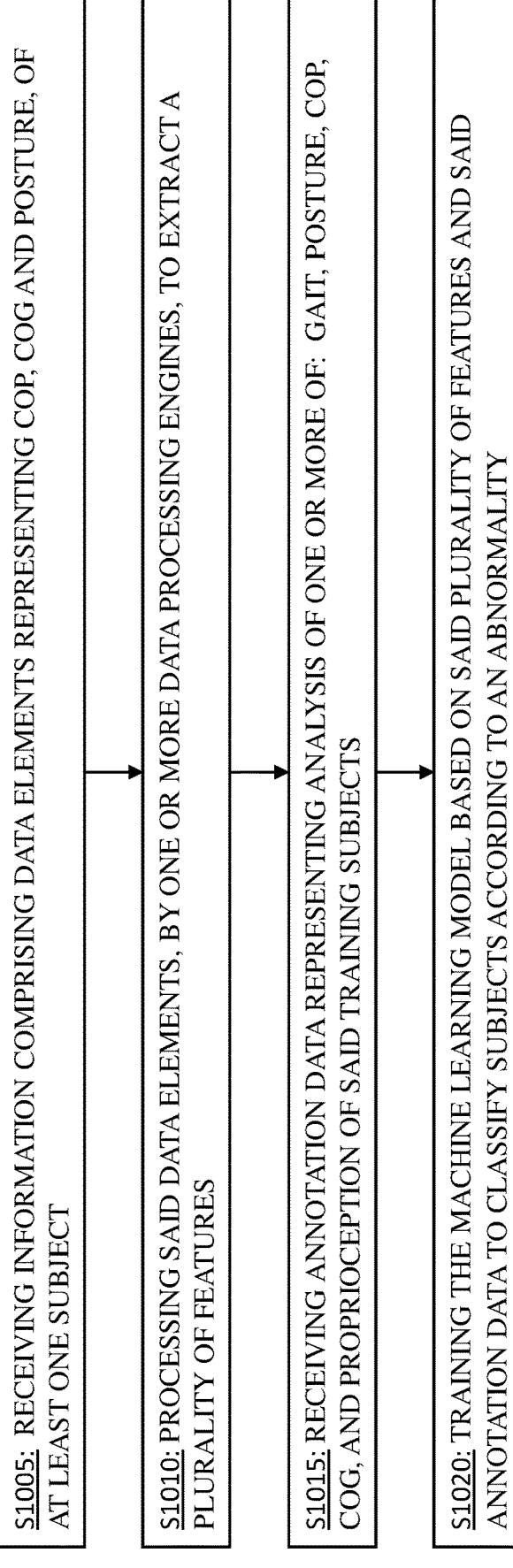

S1005: RECEIVING INFORMATION COMPRISING DATA ELEMENTS REPRESENTING COP, COG AND POSTURE, OF AT LEAST ONE SUBJECT

S1010: PROCESSING SAID DATA ELEMENTS, BY ONE OR MORE DATA PROCESSING ENGINES, TO EXTRACT A PLURALITY OF FEATURES

S1015: RECEIVING ANNOTATION DATA REPRESENTING ANALYSIS OF ONE OR MORE OF: GAIT, POSTURE, COP, COG, AND PROPRIOCEPTION OF SAID TRAINING SUBJECTS

S1020: TRAINING THE MACHINE LEARNING MODEL BASED ON SAID PLURALITY OF FEATURES AND SAID ANNOTATION DATA TO CLASSIFY SUBJECTS ACCORDING TO AN ABNORMALITY

FIG. 7A

S1005: RECEIVING INFORMATION COMPRISING DATA ELEMENTS REPRESENTING COP, COG AND POSTURE, OF AT LEAST ONE SUBJECT

S1010: PROCESSING SAID DATA ELEMENTS, BY ONE OR MORE DATA PROCESSING ENGINES, TO EXTRACT A PLURALITY OF FEATURES

S1025: APPLYING A TRAINED MACHINE LEARNING MODEL TO SAID FEATURES, TO CLASSIFY EACH OF THE ONE OR MORE TARGET SUBJECTS ACCORDING TO AN ABNORMALITY

SYSTEM AND METHOD FOR CLASSIFYING GAIT AND POSTURE ABNORMALITY

CROSS REFERENCE TO RELATED APPLICATIONS

This application a National Phase of PCT Patent Application No. PCT/IL2021/051457, having International filing date of Dec. 7, 2021, which claims the benefit of priority of U.S. Provisional Patent Application No. 63/122,020 filed Dec. 7, 2020, entitled "GAIT CLASSIFICATION USING MULTIMODAL MACHINE LEARNING", and of U.S. Provisional Patent Application No. 63/155,341 filed Mar. 2, 2021, entitled "POSTURE OPTIMIZATION VIA CENTER OF PRESSURE AND CENTER OF GRAVITY MODIFICATION USING MULTIMODAL MACHINE LEARNING", the contents of which are all incorporated herein by reference in their entirety.

FIELD OF THE INVENTION

The present invention relates to gait and posture detection and correction. More specifically, the present invention relates to improving and correcting posture, by changing a center of pressure of a user, based on machine learning algorithms.

BACKGROUND

Human gait, formally defined as human locomotion achieved through the movement of one's limbs is a fundamental and daily-occurring human function with direct implications for functionality and quality of life. A large body of academic research substantiates the interconnections between various gait abnormalities and a host of diseases and medical conditions, including developmental disorders, neurological conditions, musculoskeletal, acute and chronic conditions, and diabetes, inter alia. As an example, patients suffering from Parkinson's will exhibit gaits characterized by rigidity and slow movement, they will be stooped with their head and neck forward, and present flexion at the knees.

Postural control has been defined as the control of the body's position in space for the purposes of balance and orientation. It is based on the central integration of vestibular, visual, proprioceptive, and tactile information and on an internal representation of the body's orientation in space.

The internal model of the body's position is continuously updated on the basis of this multisensory feedback and this internal representation is used to forward motor commands controlling the body's position in space that take into account the environmental constraints (Massion J. Postural control system. Curr Opin Neurobiol. 1994; 4:877-87).

Many postural behaviors encountered in everyday situations are generally paired with cognitive performances. Indeed, it is the rule, rather than the exception, that individuals perform static- (standing) or dynamic-walking, postural tasks simultaneously with cognitive tasks.

The degeneration of the balance control system in many pathologies has forced researchers and clinicians to understand more about how the system works and how to quantify its status at any point in time. With the increase in ageing population and with increased life expectancy of our elderly the importance of maintaining mobility is becoming even more critical. Injuries and loss of life due to falls in the elderly is a very major factor facing them.

Virtually all neuromusculoskeletal disorders result in some degeneration in the balance control system. Because of the ability of the CNS to adapt for the loss of function a given pathology may not be apparent until the patient is temporarily deprived of the compensating system. Vestibular patients, for example, have excessive reliance on vision, so when they close their eyes or walk in a dark area, they become very unstable. Pathologies that have special balance challenges would include the following: chronic ankle sprains, chronic degenerative low back pain, scoliosis, paroxysmal positional vertigo, head injury, stroke, cerebellar disease, Parkinson's disease, vestibular deficits, peripheral neuropathies, amputation, and cerebral palsy.

Because of the relationship between gait abnormalities and morbidity, gait has been studied extensively, and its assessment has traditionally focused on three main areas: (1) functional limitation assessment—reflecting the impact of different diseases and supporting a diagnosis; (2) treatment efficacy assessment—where gait serves as an important outcome measure when evaluating the effectiveness of a given treatment; and (3) prediction—for both prognosis and the unfolding of underlying pathologies.

The gold standard for posture and gait analysis are 3D motion analysis systems (e.g. Vicon, Qualisys). However, these are often both cost-prohibitive and require special laboratory settings. As a result, frequently, gait analysis is performed using a combination of technologies, which vary in complexity and cost, including pressure sensors (e.g. force plates, walk mats), electromyography systems, photoelectric bars, and Inertial Measurement Units (IMU)—typically based on accelerometers and/or gyroscopes, and employed either as standalone units or sensors embedded in existing devices such as smartphones or wearable devices.

Still, all these systems rely on a single modality (e.g. vision, pressure, inertia) and fail to incorporate a wide range of available data required in order to create a patient's unique gait profile which takes into account the patient's background, and further includes a classification of the abnormality type, deviation and degree of severity.

Furthermore, existing devices may provide data regarding balance or gait, but such devices are inadequate to provide a diagnosis or suggest possible diagnosis, nonetheless, to provide corrective measures to improve posture and gait.

The foregoing examples of the related art and limitations related therewith are intended to be illustrative and not exhaustive. Other limitations of the related art will become apparent to those versed in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in an embodiment, a system comprising: at least one hardware processor; and a non-transitory computer-readable storage medium having stored thereon program instructions, the program instructions executable by the at least one hardware processor to: receive, with respect to each of a plurality of subjects, data comprising at least one of: data representing center of pressure (COP) of a subject during at least on gait phase; data representing center of gravity (COG) of said subject during at least on gait phase; and a data representing posture of said subject during at least on gait phase; receive, with respect to each of the subjects, an analysis of a gait of the subject, process the data to extract a plurality of features representing the data, at a training stage, train a machine learning model on a training set comprising all of the plurality of features, and at an inference stage, apply the trained machine learning model to a target set of the features obtained from a target subject, to classify at least one of: gait, posture, proprioception and/or kinesthesis of the target subject.

There is also provided, in an embodiment, a method comprising: receiving, with respect to each of a plurality of subjects, data comprising at least one of: a data representing center of pressure (COP) of a subject during at least on gait phase; data representing center of gravity (COG) of said subject during at least on gait phase; and data representing posture of said subject during at least on gait phase; processing the data to extract a plurality of features representing the data, at a training stage, training a machine learning model on a training set comprising all of the plurality of features; and at an inference stage, applying the trained machine learning model to a target set of the features obtained from a target subject, to classify at least one of: gait, posture, proprioception and/or kinesthesis of the target subject.

There is further provided, in an embodiment, a computer program product comprising a non-transitory computer-readable storage medium having program instructions embodied therewith, the program instructions executable by at least one hardware processor to: receive, with respect to each of a plurality of subjects, data comprising at least one of: a data representing center of pressure (COP) of a subject during at least on gait phase; a data representing center of gravity (COG) of said subject during at least on gait phase; and a data representing posture of said subject during at least on gait phase; process the data to extract a plurality of features representing the data; at a training stage, train a machine learning model on a training set comprising all of the plurality of features; and at an inference stage, apply the trained machine learning model to a target set of the features obtained for ma target subject, to classify posture, proprioception and/or kinesthesis of the target subject.

In some embodiments, the training dataset further comprises labels associated with the analysis of at least one of gait, COP, COG and posture of each of the subjects.

In some embodiments, the plurality of features are annotated or labeled with the labels.

In some embodiments, the data representing of COP, COG and posture of the subject comprises a video segment and/or sensor data.

In some embodiments, the plurality of features comprise one or more of: a gait velocity, a step length, cadence, plantar pressure distribution, gait stance, gait swing, single limb support, double limb support, gait symmetry, lower extremity range of motion, mean and max joint angle, coupling metrics, pressure distribution, COG, COP, COP trajectory, COP velocity, posture including upper extremity and lower extremity, lower extremity alignment, stride to stride variability, and gait variability over time.

In some embodiments, the clinical data comprises one or more of: gender, race, BMI, age, physical examination of joints, visual anatomy, foot alignment examination, and hyperlaxity.

In some embodiments, the clinical data comprises one or more of: history of different diseases and injuries, chronic ankle instabilities, history of ankle or other joint fractures, history of extremity fractures, history of overuse injuries, lower back pain, scoliosis, history of musculoskeletal disorders, comorbidities, regular pain medication intake, history of surgery in a lower extremity, and visual gait assessment parameters.

In some embodiments, the clinical data comprises one or more parameters reported by each of the subjects, selected from the group consisting of: degree of pain experienced, degree of functional impairment experienced, and degree of quality-of-life impairment experienced.

In some embodiments, the analysis of posture of each of the subjects comprises one or more of: faulty/imbalanced posture, posture abnormality severity, and faulty/imbalanced posture source and corrective means via alteration of COP/COG.

In some embodiments, the classifying comprises one or more of: faulty/imbalanced posture, faulty/imbalanced posture severity, source, COP/COG alterations minimizing imbalanced posture.

In some embodiments, the classifying reflects a confidence level.

In some embodiments, there is further provided clinical data received as one or more of: textual data, audio data, and visual data.

In some embodiments, at least a portion of the clinical data is received as at least one of: Electronic medical records (EMR), and electronic health record (EHR).

In some embodiments, with respect to the clinical data, the processing comprises applying a natural language processing algorithm to the received clinical data.

In addition to the exemplary aspects and embodiments described above, further aspects and embodiments will become apparent by reference to the figures and by study of the following detailed description.

BRIEF DESCRIPTION OF THE DRAWINGS

Exemplary embodiments are illustrated in referenced figures. Dimensions of components and features shown in the figures are generally chosen for convenience and clarity of presentation and are not necessarily shown to scale. The figures are listed below.

FIG. 4 is a flowchart of the functional steps in creating a machine learning model for classifying human gait, posture, COP and/or COG according to some embodiments of the present disclosure;

FIGS. 7A and 7B are flowcharts of training and inference of a machine learning model for gait and posture abnormality classification according to embodiments of the present invention.

Figure 1:
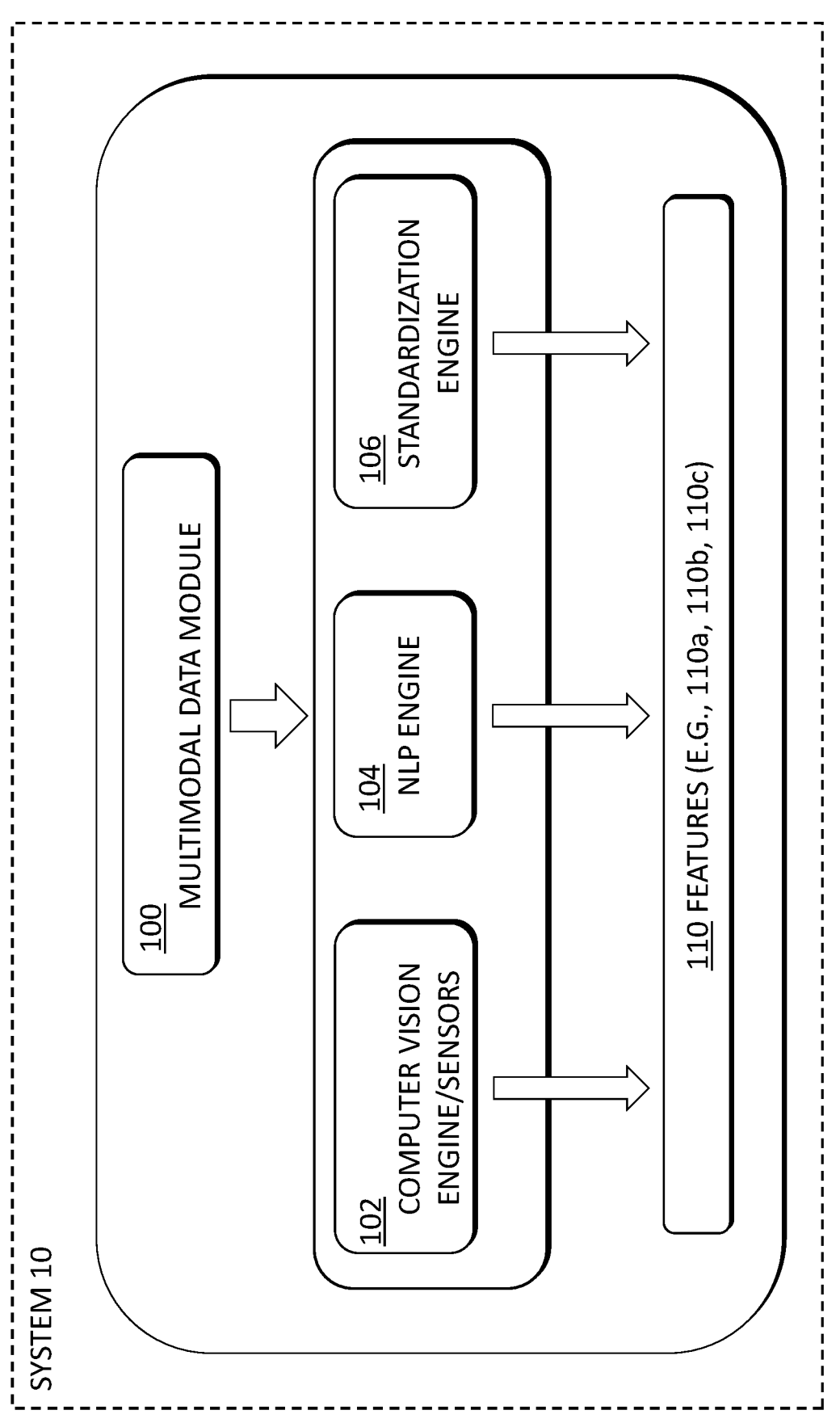
FIG. 1 shows an exemplary system for classifying human gait based on multimodal data, according to some embodiments o the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

Disclosed herein are a system, method, and computer program product for classifying proprioception, kinesthesis, balance, or any combination thereof based on multimodal data, which might include, but is not limited to, human posture, center-of-pressure (COP), center-of-gravity (COG), gait, medical history, patient-reported outcomes, visual examination, laboratory gait assessment, video gait capture, clinical assessment, and physical examination or any combination thereof.

The system and methods disclosed herein are designed to produce a machine-learned analysis and diagnosis of proprioception, kinesthesis, balance, or any combination thereof, and assess its deviation and severity in various pathologies, risks and pain related situations including musculoskeletal related pain and neurological pain, based on multimodal data points.

The system generates a machine-learned classifier that is trained to maximize the accuracy of suggested diagnoses based on available training data. This machine-learned diagnosis (including severity and deviation measures) may be employed by physicians or other caregivers to assist with their own diagnoses, as well as help them determine the causes of disease, and decide on, calibrate or predict the clinical efficacy of various treatment protocols. The system comprises two main components (i) an offline learning module, and (ii) a real-time analysis module, described in detail below.

In some embodiments, the present disclosure may be particularly useful in conjunction with the diagnosis and treatment of a lower limb joint pathology such as, but not limited to, degenerative joint diseases and musculoskeletal traumas of the lower limbs. In some embodiments, the present disclosure may be particularly useful in conjunction with the diagnosis and treatment of spinal disorders. In some embodiments, the present disclosure may be particularly useful in conjunction with the diagnosis and treatment of a gait abnormality.

In some embodiments, the present disclosure may be particularly useful in conjunction with the diagnosis and treatment of imbalance. In some embodiments, the present disclosure may be particularly useful in conjunction with the diagnosis and treatment of postural dysfunction. In some embodiments, the present disclosure may be particularly useful in conjunction with the diagnosis and treatment of painful conditions associated with poor posture such as but not limited to: low back pain, shoulder pain, arm pain, foot pain, knee pain, muscle pain or any combination thereof. In some embodiments, the present disclosure may be particularly useful in conjunction with the diagnosis and treatment of muscular and skeletal imbalance. In some embodiments, the present disclosure may be particularly useful in conjunction with protecting the supporting structures of the body against injury or progressive deformity. In some embodiments, the present disclosure may be particularly useful in the diagnosis, treatment and correction of structural postural faults that underlie many back and lower limb pathologies and pains. In some embodiments, the present disclosure may be particularly useful in the diagnosis, treatment and correction of over-pronation and over-supination. In some embodiments, the present disclosure may be particularly useful in the treatment and correction of leg length inequalities.

It is well accepted that clinical gait analysis may provide for:

Diagnoses among disease entities;

assessing the severity, extent or nature of a disease or injury;

assessing functional limitations resulting from gait abnormalities, which reflect the impact of different diseases on functionality, such as developmental disorders, neurological conditions, musculoskeletal, acute and chronic conditions, diabetes and more;

monitoring progress in the presence or absence of intervention; and predicting the outcome of intervention (or the absence of intervention) and assessing treatment efficacy.

In some embodiments, posture describes the orientation of a body segment relative to the gravitational vector. It is an angular measure from the vertical. In some embodiments, balance describes the dynamics of body posture to prevent falling. Balance, in some embodiments, is related to the inertial forces acting on the body and the inertial characteristics of body segments.

Center of gravity (COG) is the vertical projection of center-of-mass (COM). In one embodiment, this is a point equivalent of the total body mass in the global reference system (GRS) and is the weighted average of the COM of each body segment in 3D space. It is a passive variable controlled by the balance control system.

Center of pressure (COP). This is the point location of the vertical ground reaction force vector. In one embodiment, it represents a weighted average of all the pressures over the surface of the area in contact with the ground. In one embodiment, COP is totally independent of the COM. If one foot is on the ground the net COP lies within that foot. If both feet are in contact with the ground the net COP lies somewhere between the two feet, depending on the relative weight taken by each foot. In one embodiment, when both feet are in contact there are separate COPS under each foot. In one embodiment, one force platform is used only the net COP is available. In one embodiment, two force platforms are required to quantify the COP changes within each foot. In one embodiment, the location of the COP under each foot is a direct reflection of the neural control of the ankle muscles. Increasing plantar-flexor activity moves the COP anteriorly, increasing invertor activity moves it laterally. In one embodiment, its units are meters (m).

In one embodiment, posture, COP, COG or any combination thereof is/are measure while standing or while quiet standing. In one embodiment, posture, COP is measured while standing. In one embodiment, deviations in COP in both anteroposterior (A/P) and mediolateral (M/L) directions are measured and recorded as data.

Assessing balance, posture, COP, COG and/or gait deviations and classifying severity may provide for predicting optimal treatment and/or treatment timing (e.g., the point in time that will be ideal correction and/or treatment such as but not limited to reducing pain, reducing the risk of falls, correcting faulty posture, reducing a joint damage, etc. This ability may provide a patient with tangible information and assessment of their functional condition and will help the process of shared decision with the physician.

In addition, assessing balance, posture, COP, COG and/or gait deviations and classifying severity may further provide for an analysis of the likely sources of the abnormality (e.g., knee, back, hip, or other source of symptoms). In some embodiments, assessing balance, posture, COP, COG and/or gait deviations and classifying severity may further provide for remedy based on correcting the imbalance or abnormality.

Furthermore, balance, posture, COP, COG and/or gait assessment may enable determining a correct application and calibration of a foot positioning system such as but not limited to a protuberance having a ground contact surface and an outsole base.

Accordingly, in some embodiments, the present disclosure provides for assessing and classifying, posture, COP, COG and/or gait using a low-cost, readily-available mobile device-based tool for posture, COP, COG and/or gait analysis, which is simple to use, easy and quick to setup and offers high accuracy, repeatability and reliability. In some embodiments, the present disclosure provides for assessing and classifying, posture, COP, COG and/or gait using a pressure or a weight sensor. In some embodiments, the present disclosure provides for assessing and classifying, posture, COP, COG and/or gait using a weight, tilt, flow, level and/or pressure sensor. In some embodiments, the present disclosure provides for assessing and classifying, posture, COP, COG and/or gait using a camera. In some embodiments, the present disclosure provides for assessing and classifying, posture, COP, COG and/or gait using a combination of a camera and a sensor as described herein. In some embodiments, each of the camera and the sensor as described herein is in communication with a computer, directly or indirectly.

In some embodiments, the present disclosure employs a multimodal machine learning model which relies on data obtained using imaging modalities, sensor modalities (as described herein) or both and is configured for imbalance, faulty posture, a proprioception disorder, reduced kinesthetic sense, its deviation and severity. In some embodiments, the present disclosure comprises two components: (i) an offline or online learning module, and (ii) a real-time analysis and classification module.

In some embodiments, a trained posture, COP, COG or any combination thereof, machine learning model of the present disclosure may be used for initial evaluation of posture, COP, COG, proprioception and/or kinesthesia and/or abnormalities thereof and their degree of severity. In some embodiments, posture, COP, COG or any combination thereof assessment/s may be used in conjunction with treatment and/or correction device configure for treating and correcting any abnormality, imbalance, pathology and/or pain associated with faulty or imbalanced posture, COP, COG, e.g., posture, COP, COG altering/correcting device such as a correcting footwear, orthotics, and/or related devices.

In some embodiments, a trained posture, COP, COG or any combination thereof, machine learning model of the present disclosure may be used for follow-on assessment with respect to the efficacy of the treatment and any improvements precipitated in posture, COP, COG or any combination thereof. In some embodiments, a trained posture, COP, COG or any combination thereof machine learning model of the present disclosure may be used for periodic follow-up assessment with respect to the efficacy of the treatment and any improvements precipitated in posture, COP, COG or any combination thereof over time.

In some embodiments, force platforms and pressure-measuring insoles are used for measuring center of pressure (COP). In some embodiments, a device or footwear used to correct faulty or imbalanced posture, COP, and/or COG comprise a pressure-measuring insole. In some embodiments, the present invention enables the structuring and positioning of a perturbation altering the position of a foot with respect to the ground during gait or during a gait phase.

In some embodiments, a trained machine learning model of the present disclosure may be trained on a training set comprising a plurality of previously profiled and diagnosed patients, in order to produce a potential diagnosis of the gait abnormality type and assess its deviation and severity.

In some embodiments, the offline learning module takes as input patient multimodal data points (e.g., physical examination results, medical history, patient-reported outcomes, visual gait assessment, video of patient walking, etc.). in some embodiments, the offline learning module may also incorporate diagnoses provided by a medical practitioner, including classification and assessment of any orthopedic or neurological disease, pain or disorder (e.g., Chronic Ankle Instability or Knee Osteoarthritis (OA), along with severity assessment and degree of deviations).

With reference to FIG. 1, in some embodiments, a system 10, which may be or may include an offline module, may include a multimodal data module 100. Multimodal data module 100 may comprise a plurality of sensors and/or cameras, configured to collect sensors data such as COP, COG, video streams depicting motion, gait, posture and the like. According to some embodiments, multimodal data module 100 may, in addition to sensors data, or instead of sensors data, may receive, obtain or have access to, semantic unstructured data (e.g., medical history or physician notes as recorded in an Electronic medical records (EMR), and electronic health record (HER)), and structured data points (e.g. age, duration of symptoms, responses to structured questionnaires, etc.), and other subjects' related data.

According to some embodiments, the data collected or otherwise received by multimodal data module 100, may be processes by one or more of three distinct engines:

Computer vision/sensor data engine 102 which extracts features relating to spatiotemporal gait and/or posture patterns, COP COG, pressure distribution, proprioception data and alignment data;

Natural Language Processing (NLP) Engine 104 which is configured to extract semantic information from unstructured data (e.g., medical history or physician notes as recorded in an Electronic medical records (EMR), and electronic health record (HER)); and Standardization Engine 106: A module which receives all structured data points (e.g. age, duration of symptoms, etc.) and normalizes the data points.

According to some embodiments, each of engines 102, 104 and 106 may be configured to extract features 110, such as, computer vision extracted features 110a (e.g., a gait velocity, a step length, cadence, gait stance, gait swing, gait symmetry, lower extremity range of motion, mean and max joint angle, coupling metrics, stride to stride variability, gait variability over time etc.), sensors extracted features 110b (e.g., pressure distribution, COG, COP, COP trajectory, COP velocity, posture including upper extremity and lower extremity, lower extremity alignment, etc.), unstructured data features 110c (e.g., medical history, subscribed medicine, etc.) and structured data features 110d (e.g., age, gender, pain level, etc).

Figure 2:
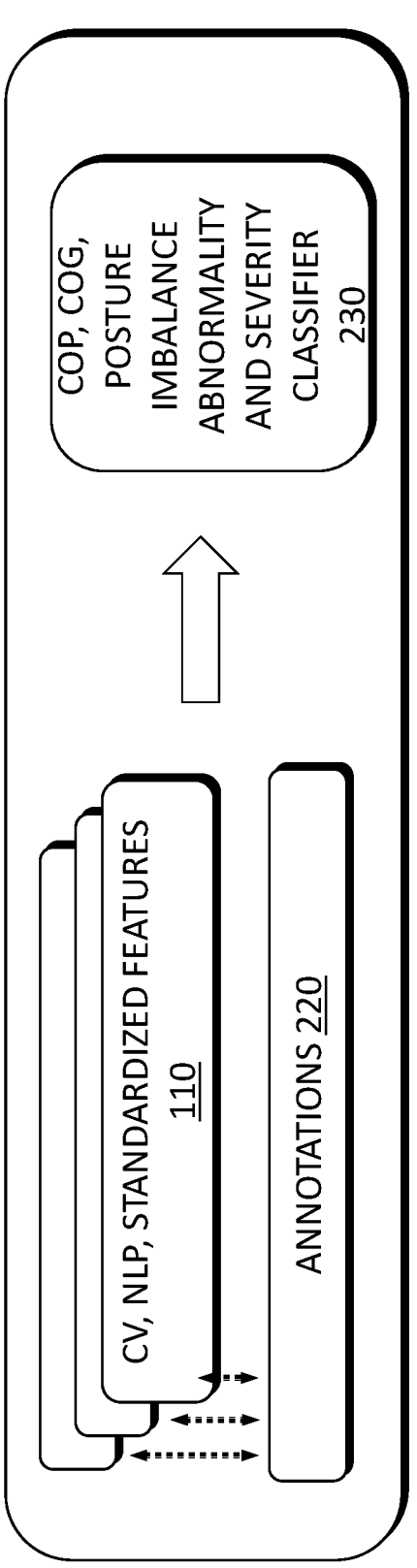
FIG. 2 schematically illustrates feature extraction process, according to some embodiments o the present invention.

With reference to FIG. 2, in some embodiments, gait-related features 110 extracted by one or more of the three engines 102, 104, 106 (in FIG. 1) may be fed together with annotations 220 (e.g., their paired diagnoses) into a machine learning algorithm (e.g. a linear classifier such as a Support Vector Machine (SVM), or a non-linear algorithm such as a Deep Neural Network (DNN), or one of its variants) to train a classifier 230 modeling gait, COP, COG, posture imbalance/abnormality with deviation and severity assessment.

Figure 3:
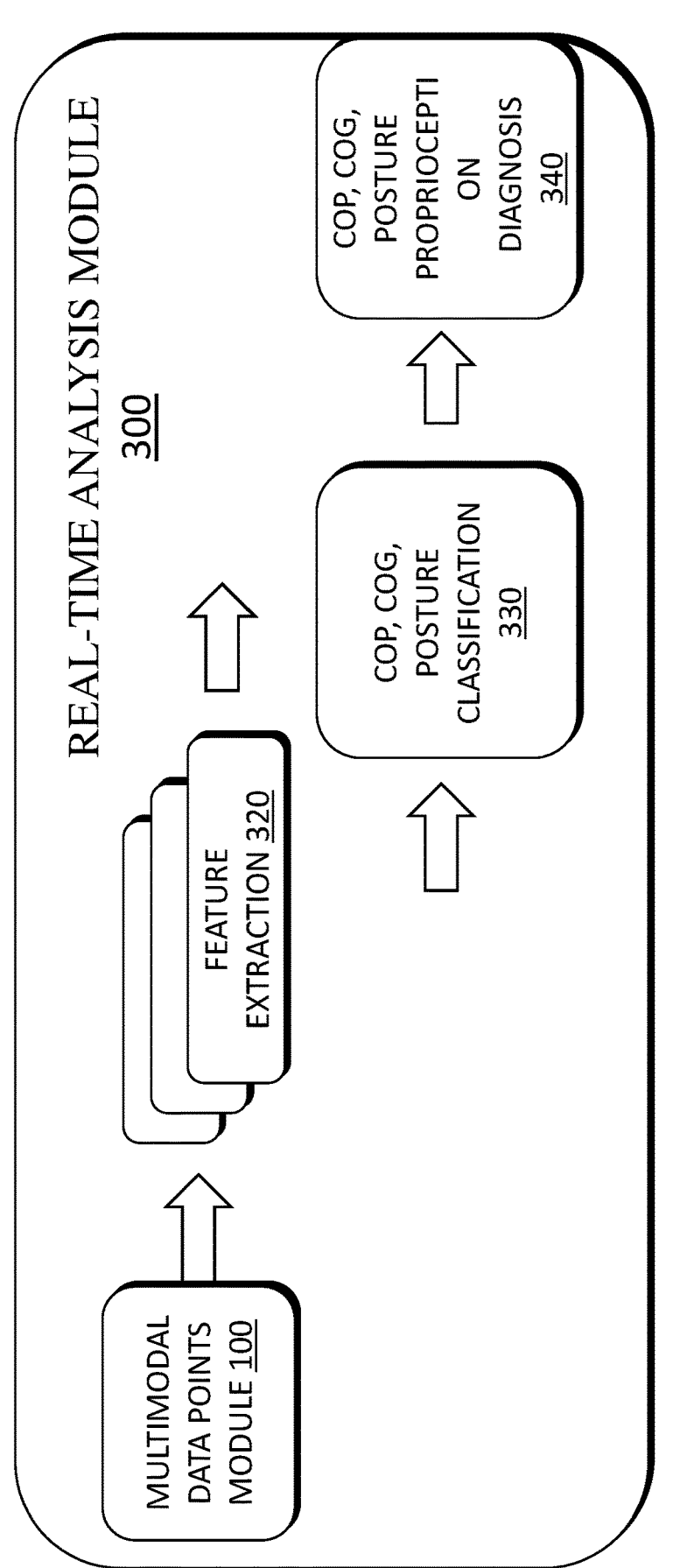
FIG. 3 schematically illustrates a machine learning model of the present disclosure, according to some embodiments o the present invention.

With reference to FIG. 3, in some embodiments, a trained machine learning model classifier of the present disclosure may be used by a real-time analysis module 300, which extracts one or more of gait, COP, COG, posture-related features 320 using the same engines as system 10 in FIG. 1, and feeds them into the trained classifier 330 to produce a posited diagnosis 340 of one or more of: gait, COP, COG, posture, and/or proprioception abnormality with deviations and severity assessment.

FIG. 4 is a flowchart of the functional steps in creating a machine learning model for classifying gait, COP, COG, and/or posture, according to some embodiments of the present disclosure. In some embodiments, the present disclosure provides for training a machine learning model on a training set comprising multimodal data points, as described above.

Data Gathering

In some embodiments, at step 400 in FIG. 4, a multimodal data module 100 shown in FIG. 1 of the present disclosure may be configured for receiving and/or obtaining a plurality of data points from a plurality of sources (e.g., camera(s) and/or other sensors, databases, EMR, etc.). In some embodiments, the plurality of data points may be associated with a cohort of subjects.

In some embodiments, data sources may include audio, transcripts, written notes and sketches, EMR/EHR files (electronic or printed), photos, video, digital files or any other formats of digital output by designated laboratory equipment, databases, or any other means of storing data. In some embodiments, such data points may be obtained as structured data (e.g., as predetermined fields in an EMR/EHR) or unstructured language or visual data (e.g. text, audio, photo or video). The data may be received from one or more sensors such as pressure sensors, image sensors, audio sensors, and the like.

In some embodiments, a training set of the present disclosure may comprise data points associated with one or more of:

Visual Posture and/or Gait Assessment including for example, multi-angle foot view, ankle, spine, abdomen, trunk, shoulders, hands, legs. Neck, head, knee or hip and lateral view of ankle, knee or hip, as well as posture in general and upper extremities, symmetry;

Laboratory and Device-Generated Gait Assessment: Spatiotemporal metrics, such as velocity, step length, cadence, gait cycle phases (stance, swing, single limb support, double limb support), symmetry, e.g., differences between left and right sides, base of support, and toe-in/out angle.

COP/COG Assessments and Plantar Pressure Distribution: data relating to the distribution of force over the plantar area of the foot, COP during standing, COP trajectory during walking, and COG;

Video Recordings: Video capture of gait, posture in at least one position using a variety of setups (e.g., multiple cameras setup, simple standalone cameras, or mobile phone cameras), symmetry and difference between left and right sides, and any other metric such as degree of flexion, neck and head posture, etc.;

Physical Examination and Other Personal Data: Gender, race, BMI, age, physical examination of joints, visual anatomy (e.g. varus, valgus), foot alignment examination, hyperlaxity examination, inter alia;

Medical History: Personal and/or family history of different diseases and injuries, chronic ankle instabilities, history of ankle or other joint fractures, history of extremity fractures, history of overuse injuries, lower back pain, scoliosis, other medical histories related to musculoskeletal disorders, comorbidity, regular pain medication intake, other medications, previous surgery in the lower extremity;

Primary and Secondary Complaints: Duration of symptoms, surgery and other treatment recommendations;

Patient-Reported Outcomes: Subjective disease severity as determined by pain, function, and quality of life collected either using self-evaluation questionnaires or in sessions with caregivers;

Detailed Treatment Protocols Applied to the Patient: Any medical intervention such as surgery, medications, physiotherapy, corrective biomechanical aids, footwear and/or AposTherapy®, etc.;

Other Data Received from Designated Devices: such as sensors (weight, tilt, flow, level and/or pressure sensor), sensors embedded within footwear, the perturbation positioning; Along with the data points, system 10 (in FIG. 1) may take in human diagnoses paired with the patient data, which may include classification and severity assessment as well as degree of deviations. For example, such diagnoses can include any instability manifested in imbalanced COP, COG and/or posture inclusive of: any lower limb pathology such as but not limited to knee Osteoarthritis, any neurological pathology such as but not limited to Parkinson's disease. Additional human diagnoses may further include gait assessment such as hemiplegic gait, spastic diplegic gait, neuropathic gait, myopathic gait, Parkinsonian gait, choreiform gait, ataxic (cerebellar) gait and sensory ataxic gait. All diagnoses may include a severity assessment as well as degree of deviations.

Data Analysis

In some embodiments, at step 402 in FIG. 4, a multimodal data module 100 of the present disclosure may be configured to assign data points to one or more data processing modules of the present disclosure, such as engines 102, 104 and 106 in FIG. 1, for processing and analysis.

In some embodiments, the multimodal data module 100 may be configured to process the data points using one or more of three distinct engines, as shown in FIG. 1. In some embodiments, a first data processing engine may comprise an image processing and/or computer vision engine and/or sensor data engine 102, configured to process image data or sensor data obtained from e.g., a video stream, a sensor or an array of sensors and extract posture, COP, COG, proprioception and kinesthesis features relating to spatiotemporal gait, posture, and patterns and metrics such as, but not limited to:

velocity, step length, cadence, gait cycle phases (stance, swing, single limb support, double limb support),

COP,

COG, static posture measure, back shape assessment, flexiruler for the evaluation of posture, symmetry and difference between left and right sides, two-dimensional evaluation of posture, three-dimensional evaluation of posture,
photogrammetric postural evaluation,
Posturometer-S measure,
ordinal scales,
goniometry,
measurement of distance between bony points,
degree of flexion, and/or
neck and head posture.

In some embodiments, the computer vision/sensor data engine 102 may receive a video stream or a sequence of images from one or more cameras configured to capture gait and/or posture of a subject and analyze a wide spectrum of features associated with the captured gait and/or posture. In some embodiments, the computer vision/sensor data engine 102 may receive a sequence of sensor reads configured to capture, COP, and/or COG of a subject, and analyze a wide spectrum of features associated therewith. In some embodiments, the computer vision/sensor data engine 102 uses both camera derived data and sensor derived data.

Vision-based motion analysis involves extracting information from sequential images in order to describe movement or a multi-component structure. Optical analysis according to the invention, includes estimation of the position and orientation (pose) of a subject, a set of objects or an area of a subject's body, across image sequences. Through the identification of common object features or the identification of matching positions in successive images, displacement data can be tracked over time or over an area to be imaged. However, accurate quantification of whole-body pose can be a difficult problem to solve since the human body is an extremely complex, having multiple planes and is highly articulated, self-occluding and only partially rigid.

In some embodiments, the computer vision/sensor data engine 102 of the present disclosure may be configured for analyzing in-depth gait, posture, kinesthesis, and/or proprioception including spatio-temporal, kinematic and kinetic parameters, such as joint and skeletal spatial position, limbs angles, stride length and width, trunk, and head/neck spatial position, among others.

In some embodiments, the present disclosure may comprise a marker-based system wherein a number of reflective markers may be attached to several key points of the patient's body and then captured by imaging sensors fixed at known positions in the footage environment such as but not limited to bony points. The markers positions are then transformed into 3D positions or postures using triangulation from the several feeds (e.g., cameras, other sensors, and the like).

In some embodiments, the present disclosure may employ a marker-less body posture and/or gait capture system, e.g., based on an articulated-model approach. A marker-less approach to posture and/or gait (or motion) capture does not require subjects to wear special equipment for tracking. Special computer algorithms are designed to allow the system to analyze multiple streams of optical input and identify human forms, breaking them down into constituent parts for tracking. In some embodiments, a computer vision/sensor data engine 102 of the present disclosure may be configured to analyze a captured image stream to extract the subject's pose, posture, COP, COG and motion.

In some embodiments, a posture/proprioception/kinesthesis capture and analysis module of the present disclosure may be based on, e.g., inertial capture technology, using inertial sensors, biomechanical models and sensor fusion algorithms.

The inertial sensors may comprise inertial measurement units (IMUS) such as a gyroscope, a magnetometer, a pressure sensor, a weight sensor, and an accelerometer, to measure COP, COG, posture, position, and rotational rates. In some embodiment, data received from sensors and camera may be translated to a skeleton model.

Much like optical markers, the more IMU sensors the more natural the data. No external cameras, emitters or markers are needed for relative COP, COG, posture, position, motion and rotational rates, although they may be required to give the absolute position of the user if desired. Inertial motion capture systems capture the range of a body part of a human and can provide information.

In some embodiments, a motion capture and/or posture capture and analysis module of the present disclosure may be based on, e.g., mechanical capture systems which directly track body joint angles, e.g., exoskeleton structure and capture systems.

In some embodiments, a posture capture and analysis module of the present disclosure may be based on, e.g., sensors, magnetic systems which calculate position, relative positions of body parts and orientation by, for example, the relative magnetic flux.

In some embodiments, Natural Language Processing (NLP) engine 104 of the present disclosure may be configured to extract semantic information from unstructured data (e.g. medical records or physician notes as recorded in an EHR/EMR).

In some embodiments, NLP engine 104 may receive its input either directly as text from written notes or notes stored in an EHR/EMR or through a transcription of audio recorded by a physician or other caregiver. From this text it produces various semantic features including but not limited to:

Identification and extraction of topics;

identification and extraction of diagnoses;

identification and extraction of pain indication;

identification and extraction of personal data (such as gender, race, BMI, age);

identification and extraction of a physical examination and other examination reports (e.g., foot alignment examination, hyperlaxity examination, etc.);

identification and extraction of medical history, including history of different diseases and injuries (e.g. chronic ankle instabilities, history of ankle or other joint fractures, history of extremity fractures, history of overuse injuries, lower back pain, scoliosis);

identification and extraction of other medical histories related to musculoskeletal disorders, comorbidity, regular pain medication intake, medications, previous surgeries;

identification and extraction of primary and secondary complaints including duration of symptoms, surgery and other treatment recommendations;

identification and extraction of patient-reported outcomes including subjective disease severity as determined by pain, function, and quality of life either using self-evaluation questionnaires or oral interviews;

identification and extraction of Named Entity Recognition (NER);

identification and extraction of relations between entities;

identification and extraction of treatments; and/or identification and extraction of key phrases and keywords (either predetermined, or identified using a salience heuristics such as TF-IDF).

Additional features that may be extracted by the NLP engine 104 may be, for example, summarizations and various Natural Language entailments. NLP features might be extracted separately for each caregiver or for the patient themselves.

Data Standardization

In some embodiments, at step 404 in FIG. 4, a standard-ization engine 106 (in FIG. 1) of the present disclosure receives all structured data points and normalizes them. These data points may include any data stored in EHR/EMR fields or given in structured notes or databases. Examples include gender, race, BMI, structured questionnaire answers, medical charts, clinical coding of diseases and medical conditions, coding of medications and treatments, coding of any devices used in assessment or treatment, and any other structured data that lends itself to codification, such as CPT codes.

In some embodiments, standardization engine 106 may be configured to receive different sources of data feeds and converts then into a common representation. In some embodiments, a joint representation from multiple sources may be generated using, e.g., a neural network which encode or convert each data source into a representation that pre-serves most of the original data while making sure that the encoding from the different sources standardized across the different sources.

Constructing a Training Dataset

In some embodiments, at step 406 in FIG. 4, a training dataset of the present disclosure may be constructed, com-prising:

(i) Features extracted and standardized in steps 402 and 404 in FIG. 4 with respect to each subject in the cohort, and (ii) labels associated with one or more of: gait, COP, COG, posture, proprioception, and/or kinesthesis assessment of each subject in cohort.

In some embodiments, some or all features extracted by engines 102, 104, 106, may be used for constructing a training dataset for a machine learning model, to train a classifier modeling gait, posture, proprioception, and/or kin-esthesis imbalance and/or abnormality with deviation and severity assessment.

In some embodiments, not all features may be extracted for a given subject in the cohort.

In some embodiments, labels associated with a gait, posture, COP and/or COG assessment of each subject in cohort may comprise one or more of:

posture, proprioception, and/or kinesthesis abnormality type, posture, proprioception, and/or kinesthesis abnormality severity, posture, proprioception, and/or kinesthesis abnormality degree of deviation, gait abnormality type, gait abnormality severity, gait abnormality degree of deviation, predicted source of abnormality (e.g., neurological, liga-ment based, neuromuscular, muscular, skeletal, organ or organs involved or any other source of pathology, pain, imbalance and/or symptoms), one or more other diagnosed conditions.

Training a Machine Learning Model

In some embodiments, at step 408 in FIG. 4, a machine learning algorithm may be trained on the training dataset constructed at step 406 in FIG. 4, to create a machine learning model classifier of the present disclosure.

The machine learning algorithm may be any linear clas-sifier such as a Support Vector Machine (SVM), or a non-linear algorithm such as a Deep Neural Network (DNN), or one of its variants. Additional non-supervised and semi-supervised machine learning algorithms may be employed to assist training, taking advantage of troves of clinical data and other data points not directly paired with a human diagnosis, or in cases in which human diagnosis lacks components (e.g. a diagnosis that includes abnormality type but not severity or degree of deviation). Semi-super-vised machine learning algorithms may be employed to label data points with a posited diagnosis which may or may not undergo human validation. Unsupervised machine learning algorithms may be employed to cluster abnormalities and conditions and may or may not undergo human validation before being incorporated into the model.

Machine Learning Model Inference

In some embodiments, at step 410 in FIG. 4, a trained machine learning model of the present disclosure may be applied to a target set of gait, COP, COG, posture, proprio-ception, and/or kinesthesis related features obtained from a target subject, to classify gait, posture, proprioception, and/or kinesthesis of the subject. In some embodiments, the present machine learning model may be configured to clas-sify gait, posture, proprioception, and/or kinesthesis based on one or more category classes of abnormality associated with gait, posture, proprioception, and/or kinesthesis imbal-ance and/or abnormality type and a severity assessment thereof. In some embodiments, the present machine learning model may be configured to predict a likely source of the classified gait, posture, proprioception, and/or kinesthesis imbalance and/or abnormality. In some embodiments, the prediction may include a confidence level.

Accordingly, in some embodiments, a machine learning model of the present disclosure may be used for assessing posture, proprioception, and/or kinesthesis deviations and classifying severity of known conditions, e.g. scoliosis, and monitoring the alterations/changes over time.

In some embodiments, another potential application of the present machine learning model may be predicting an opti-mal treatment intervention, for example, predicting the point in time that will be optimal for a surgery (i.e. when reha-bilitation will be most effective).

In some embodiments, another potential application of the present machine learning model may be informing patients by providing tangible assessments of a patient's functional condition thus helping in the process of a shared decision with the doctor.

In some embodiments, another potential application of the present machine learning model may be the identification of a source of gait, posture, proprioception, and/or kinesthesis imbalance and/or abnormality.

In some embodiments, another potential application of the present machine learning model may be to assist with proper COP and/or COG calibration altering faulty and/or imbal-anced posture, proprioception, and/or kinesthesis and/or use of correcting footwear, orthotics, and/or similar devices for calibrating COP and/or COG.

In some embodiments, another potential application of the present machine learning model may be to predict a clinical efficacy of different treatment interventions based on COP, COG and/or posture profile and considered treatment.

Figure 5:
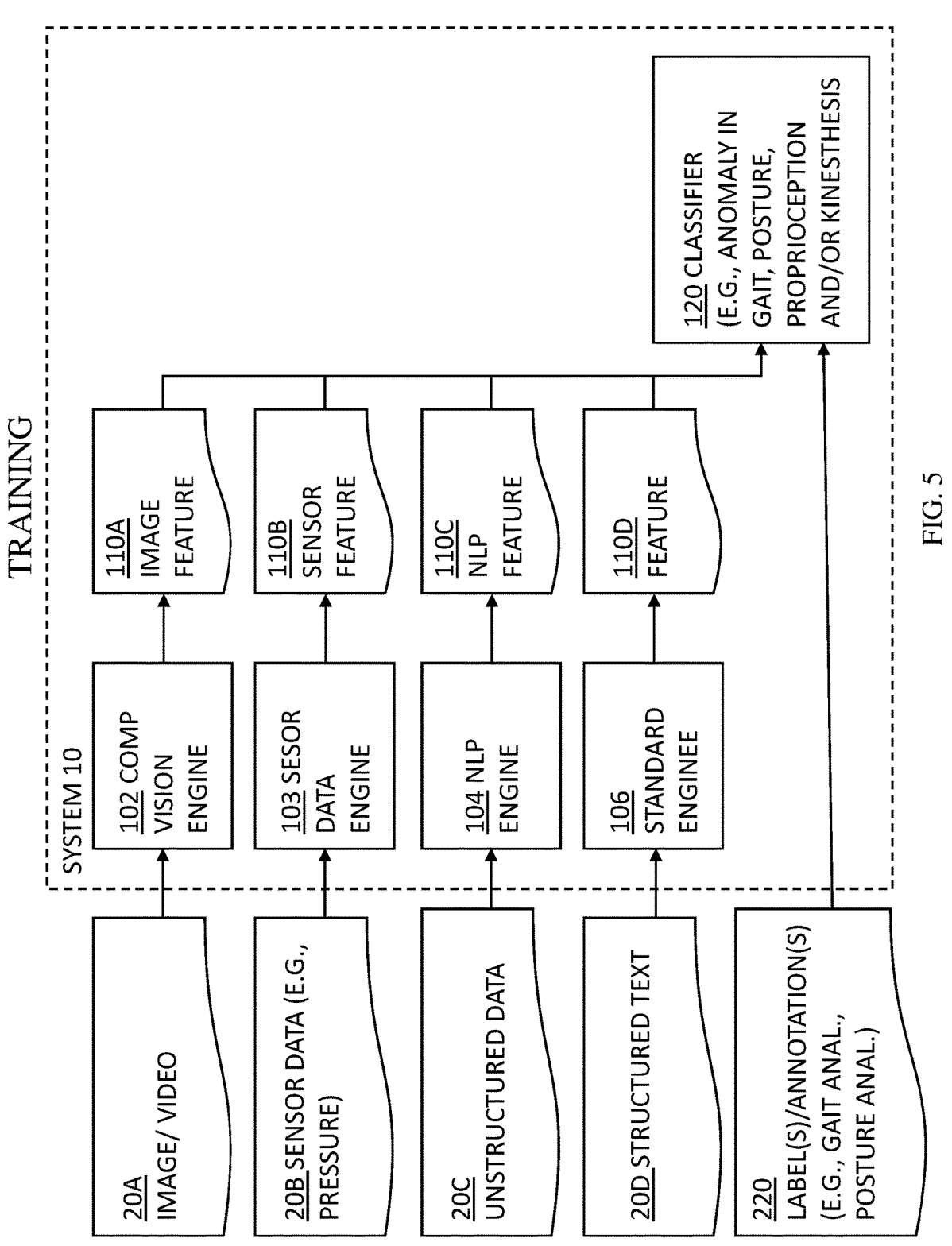
FIG. 5 is a block diagram of a system in a training stage of a machine learning model for classifying anomaly in gait, posture, proprioception and/or kinesthesis, according to some embodiments of the present invention.

Reference is now made to FIG. 5 which is a block diagram of training stage of system 10 as a classifier 120 configured to classify extracted features 110A, 110B, 110C and 110D to abnormality in gait, posture, proprioception and/or kines-thesis. As shown in FIG. 5, image and/or video data, may be obtained by one or more video/image sensors (e.g., camera (s)) and provided to computer vision engine 102, which, in turn, may extract image related features 110A from the provided footage.

Similarly, sensors data 20B collected by one or more sensors, such as pressure sensors, audio sensors, and the like, may be provided to sensor data engine 103, which in turn may extract sensor related features 110B, such as COP, COG and the like. It should be appreciated by those skilled in the art that while in FIG. 5 computer vision engine 102 and sensor data engine 103 are illustrated as separate modules, these modules may be provided in a single engine as illustrated in FIG. 1. Similarly, all or some of the engines 102, 103, 104 and 106 may be encompassed in a single module, or a combination of two or more engines may be used.

According to some embodiments, unstructured data 20C may be feed to NLP engine 104, which may be configured to extract NLP related features 110C.

According to some embodiments, structured data 20D may be feed to standardizing engine 106, which may be configured to extract features 110D such as age, gender, and the like, from structured data 20D.

According to some embodiments, some or all of the extracted features 110A, 110B, 110C, 110D may be feed to classifier 120, together with label(s) 30 such as gait analysis, posture analysis and the like.

Figure 6:
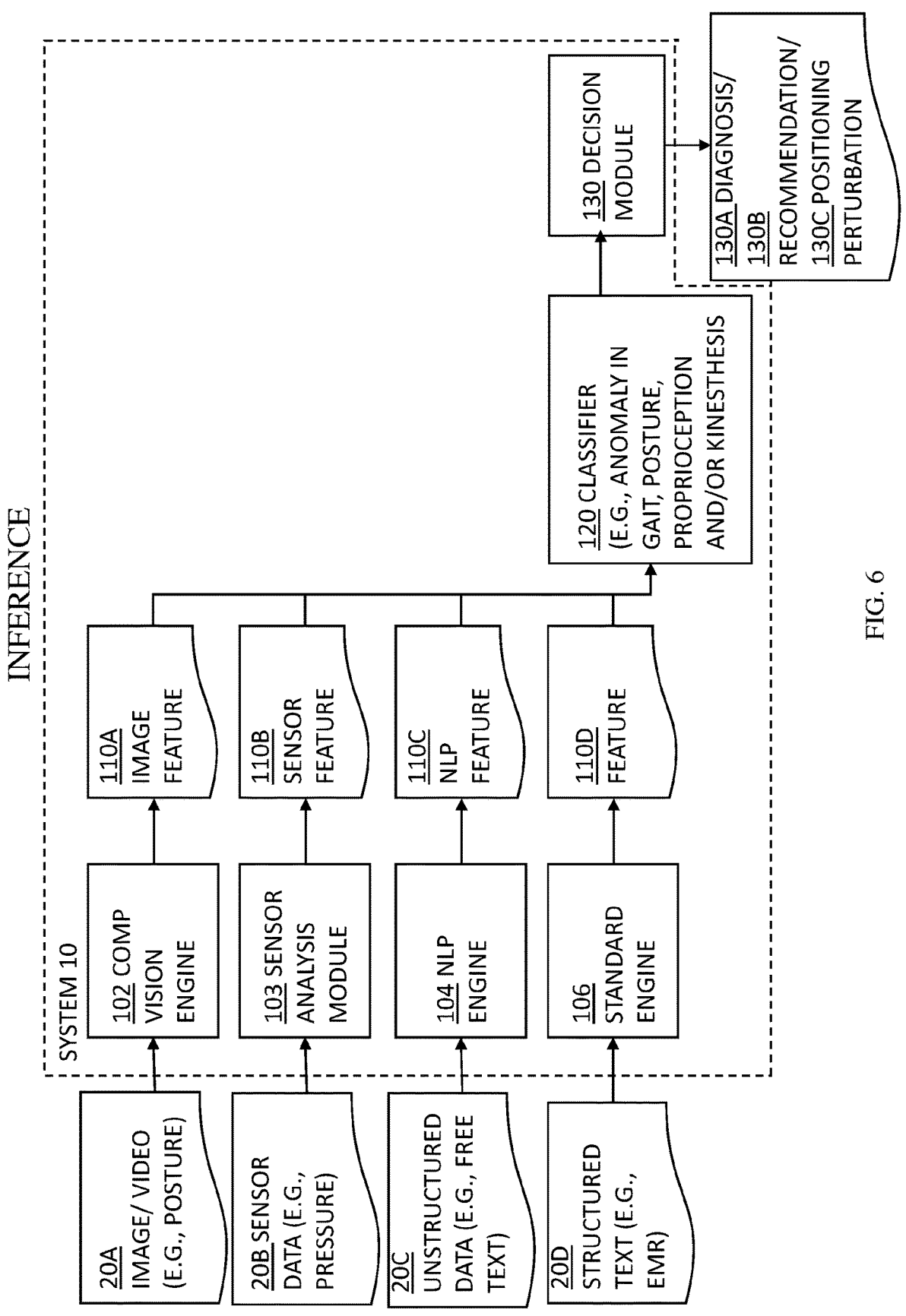
FIG. 6 is a block diagram of a system at an inference stage of a trained machine learning model, according to some embodiments of the present invention.

With reference to FIG. 6, a block diagram of system 10 in an inference stage, according to some embodiments of the present invention, is illustrated. Image and/or video data, may be obtained by one or more video/image sensors (e.g., camera(s)) and provided to computer vision engine 102, which, in turn, may extract image related features 110A from the provided footage.

Similarly, sensors data 20B collected by one or more sensors, such as pressure sensors, audio sensors, and the like, may be provided to sensor data engine 103, which in turn may extract sensor related features 110B, such as COP, COG and the like. It should be appreciated by those skilled in the art that while in FIG. 5 computer vision engine 102 and sensor data engine 103 are illustrated as separate modules, these modules may be provided in a single engine as illustrated in FIG. 1. Similarly, all or some of the engines 102, 103, 104 and 106 may be encompassed in a single module, or a combination of two or more engines may be used.

According to some embodiments, unstructured data 20C may be fed to NLP engine 104, which may be configured to extract NLP related features 110C.

According to some embodiments, structured data 20D may be fed to standardizing engine 106, which may be configured to extract features 110D such as age, gender, and the like, from structured data 20D.

According to some embodiments, some, or all of the extracted features 110A, 110B, 110C, 110D may be feed to a trained classifier 120 that is configured to classify gait, posture, proprioception, and/or kinesthesis based on one or more category classes of abnormality associated with gait, posture, proprioception, and/or kinesthesis imbalance and/or abnormality type and a severity assessment thereof. In some embodiments, decision module 130 may be configured to predict a likely source of the classified gait, posture, proprioception, and/or kinesthesis imbalance and/or abnormality. In some embodiments, the prediction may include a confidence level.

According to some embodiments, decision module 130 may provide a diagnosis 130A of gait, posture, COP and/or COG abnormalities, and/or may provide recommendations 130B for treatment and/or corrective measures. The recommendations may be based, for example, on a target subject's current COP and/or any other feature 110A, 110B, 110C and/or 110D, and the diagnosis 130A and/or identified abnormality (e.g., gait abnormality, posture abnormality and the like). The recommendation 130B may be for specific activity, treatment (e.g., medication, surgery or any other medical and/or rehabilitation interventions) physiotherapy, corrective biomechanical aids, footwear, AposTherapy®, etc.

According to some embodiments, decision module 130 may provide a recommended perturbation positioning 130C, based on the diagnosis 130A or based on, for example, the provided target subject's COP, COG, posture, and the like.

Figure 7B:
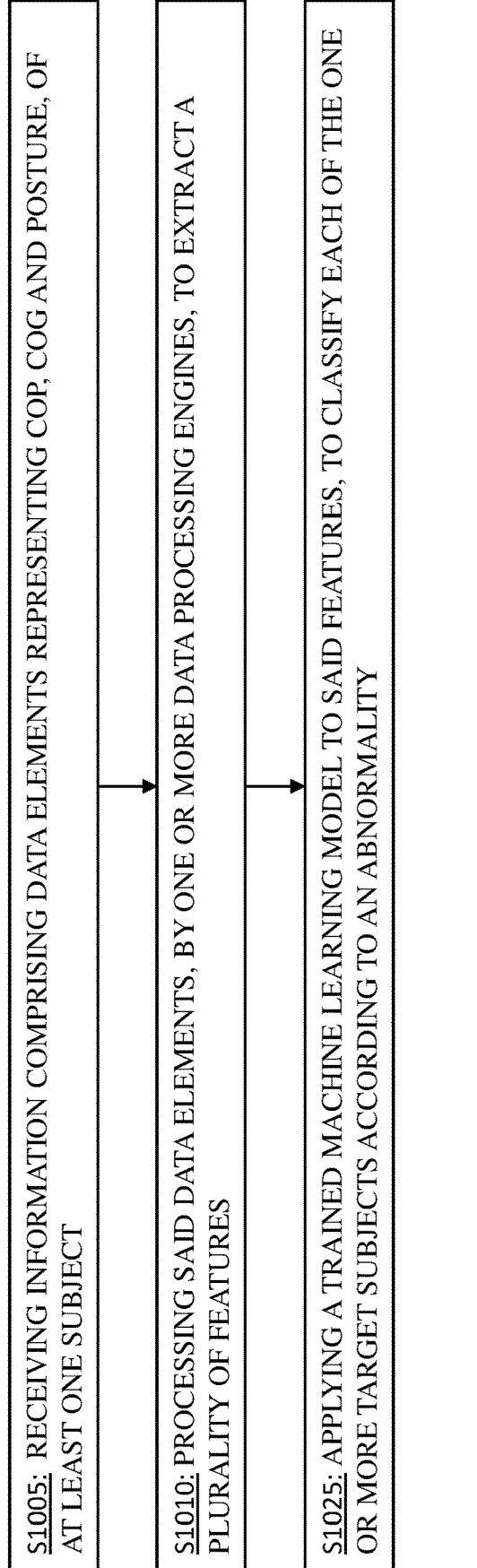

Referring now to FIGS. 7A and 7B, flowcharts of a method of training (FIG. 7A) and inference (FIG. 7B) of a machine learning model, for classifying abnormalities are provided. In step 1005, according to some embodiments, one or more data processing engines, such as engines 102, 103, 104 and 106 (in FIGS. 1, 5 and 6) may receive from multimodal data module 100 (in FIG. 1) information, e.g., in the form of video, audio, text, and the like. The information may include at least one of: (i) at least one data element representing center of pressure (COP) of a subject; (ii) at least one data element representing center of gravity (COG) of said subject; and (iii) at least one data element representing posture of said subject. At a training stage, the information may be received for a plurality of subjects (e.g., training subjects), and at the inference stage information of at least one subject (e.g., target subject) may be received.

At step 1010, the received data elements, may be processed by one or more data processing engines, such as computer vision engine 102, sensor data engine 103, NLP engine 104 and/or standardization engine 106 to extract a plurality of features representing information.

As illustrated in Step 1015 in FIG. 7A, at a training phase, annotation data representing analysis of one or more of: gait, posture, COP, COG, and proprioception of said training subjects, may be received, and a machine learning model may be trained based on the plurality of extracted features and the annotation data (Step 1020).

As may be seen in Step 1025 in FIG. 7B, at an inference phase, the trained machine learning model may be applied to extracted features of one or more target subjects and classify each of the one or more target subjects according to an abnormality, such as, for example one or more of: gait abnormality, gait abnormality severity, gait abnormality source, posture abnormality, posture abnormality severity, posture abnormality source and a proprioception disorder.

According to some embodiments, based on the classification, a decision module, such as decision module 130 in FIG. 6, may provide diagnosis 130A, treatment recommendations 130B, perturbation positioning 130C and the like.

According to some embodiments, the annotated data is used as supervisory data in the training phase.

According to some embodiments, the at least one data element representing COP, the at least one data element representing COG and the at least one data element representing posture are received from one or more sensors, such as a weight or pressure sensors, an imager, and the like.

According to some embodiments the plurality of features comprises one or more of: a gait velocity, a step length, cadence, plantar pressure distribution, gait stance, gait swing, single limb support, double limb support, gait symmetry, lower extremity range of motion, mean and max joint angle, coupling metrics, pressure distribution, COP trajectory, COP velocity, posture including upper extremity and lower extremity, lower extremity alignment, stride to stride variability, and gait variability over time.

In yet another embodiment, the information may further include one or more clinical data elements, such as, for example, one or more of gender, race, BMI, age, physical examination of joints, visual anatomy, foot alignment examination, hyperlaxity, history of different diseases and injuries, chronic ankle instabilities, history of ankle or other joint fractures, history of extremity fractures, history of overuse injuries, lower back pain, scoliosis, history of musculoskeletal disorders, comorbidities, regular pain medication intake, history of surgery in a lower extremity, and visual gait assessment parameters.

The clinical data may further or alternatively include, one or more parameters reported by the subjects, the parameters may be selected from a group consisting of: degree of pain experienced, degree of functional impairment experienced, and degree of quality-of-life impairment experienced.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a hardware processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

This invention provides, in some embodiments, a method of treating a subject suffering from a neurological/orthopedic disorder/condition or pain comprising calibrating a footwear reducing or perfecting an imbalance according to the machine learning model of the present disclosure. In one embodiment, reducing or perfecting an imbalance comprises structuring and pacing and/pr positioning a protuberance which alters a foot of a subject to an induced position which reduces or perfects an imbalance according to the machine learning model of the present disclosure.

In another embodiment, the present invention provides a method of alleviating pain, improving gait and/or balance in a subject comprising calibrating a footwear reducing or perfecting an imbalance according to the machine learning model of the present disclosure.

For example, the methods and systems disclosed herein, can improve balance of a subject afflicted with any condition which is associated with imbalance posture, proprioception and/or kinesthesis via improved muscle coordination, motor learning, normalized gait pattern, desired alignment of the joints in the lower limb and low back, and posture alignment and balancing.

For example, the methods and systems disclosed herein can improve dysmetria of a subject, via mechanism of brain plasticity, motor learning, improved and more precise proprioception and interpretation of proprioceptive and vestibular input as well as improved muscle coordination and/or neurological coordination of a subject.

For example, the methods and systems disclosed herein can reduce muscle tone of a subject having a neurological condition, via desired alignment of the joints in the lower limb and low back, reduced muscle bracing as a response to alteration of COP, COG or both via a correctional perturbation. For example, the methods and systems disclosed herein can reduce the energy cost of gait of a subject afflicted with imbalanced o faulty posture, via improved muscle coordination, motor learning, normalized gait pattern, desired alignment of the joints in the lower limb and low back. For example, the methods and systems disclosed herein can increase neuronal sprouting of a subject, via repetitive stimulation of a desired movement pattern and repeated muscular activation through alteration of COP, COG or both.

For example, the methods and systems disclosed herein can increase posture plasticity of a subject. For example, the methods and systems disclosed herein can prevent joint pain, deformity and contractures (both in the joint and various muscles) of a subject, via alteration of COP, COG or both and redistribution of loads in the joints, improved muscular activity and reduced muscle tone. For example, the methods and systems disclosed herein can prevent falls of a subject, via improved balance, improved proprioception/kinesthesis, reduced muscle tone, improved dysmetria, improved alignment and posture.

In some embodiments, the methods disclosed herein are directed to methods of improving the control over gait function. In some embodiments, the methods disclosed herein are based on the unexpected discovery that by changing the center of pressure (COP) and/or COG with which the foot contacts the ground, various posture/proprioception/kinesthesis related conditions and imbalances can be treated, improved and/or completely cured. In another embodiment, changing the center of pressure (COP) and/or COG with which the foot contacts the ground is executed through calibrating the device (such as but not limited to footwear) of the invention. In another embodiment, COP and/or COG is changed or altered via a perturbation induced by a protuberance as disclosed herein.

In another embodiment, a device of the invention alters COP and/or COG thus changing the posture and/or movement pattern. In another embodiment, the methods and systems of the invention provide a controlled change in posture pattern and concomitantly avoiding damage, injury, trauma, or a combination thereof (such as but not limited to: falls, damaging gait, damaging lower limb neuromuscular control or activity) to the subject using the device, thus efficiently enabling the accomplishment of the methods provided herein by correcting imbalance as disclosed herein.

In another embodiment, methods and systems of the present invention to strengthen various muscles and improve imbalanced posture/proprioception/kinesthesia. In some embodiments, the exercises comprise standing. In another embodiment, methods of the present invention are suitable to any person that can walk to any extent. In other words, methods of the present invention are suitable to any person suffering from or afflicted with faulty or imbalanced posture/proprioception/kinesthesis, which still can walk. In some embodiments, methods of the present invention are suitable to a person that can stand.

In some embodiments, the device of the invention may be used in the methods disclosed herein due to the ability of the device to change the foots' point of contact with the ground and COP/COG, thereby altering the forces and moments acting on the entire leg (and entire body) in any weight bearing activity and thereby balancing or improving posture/proprioception/kinesthesia.

Weight bearing activities are activities where the weight of the body is placed on the feet, such as walking, standing, getting up from a chair, and the like. In some embodiments, the device comprises at least one perturbation which integrates a shift in COP/COG into any weight bearing activity.

Specifically, a device as described herein includers two protuberances wherein the anterior protuberance and/or the posterior protuberance, are structured and positioned along the innersole or the outsole of the footwear such that COP/COG are altered and thereby reduce any instability as described herein.

In another embodiment, the methods of the invention provide that the subject wearing the device performs (daily) activities such as, for example, but not limited to: walking, standing, cooking or getting up from a chair with the device worn on both feet. In some embodiments, the device comprises 2 units of footwear: one for the left foot and one for the right foot. In another embodiment, each unit of the device comprises at least two protuberances wherein only the protuberances are ground engaging during activities such: walking, standing, cooking or getting up from a chair with the device worn on both feet. In another embodiment, each unit of the device comprises at least two protuberances wherein predominantly the protuberances are ground engaging during activities such: walking, standing, cooking or getting up from a chair with the device worn on both feet.

In another embodiment, predominantly is over 50% of the ground engaging period. In another embodiment, predominantly is over 60% of the ground engaging period. In another embodiment, predominantly is over 70% of the ground engaging period. In another embodiment, predominantly is over 80% of the ground engaging period. In another embodiment, predominantly is over 90% of the ground engaging period. In another embodiment, predominantly is over 95% of the ground engaging period.

In another embodiment, ground engaging period is the period in percent of the gait cycle wherein part of the footwear is in contact with a ground surface. In another embodiment, ground engaging period is the period in percent of the gait cycle wherein part of the footwear is in contact with a ground surface during gait and/or stance.

As referred to herein, the term "walking" is directed to spatial movement of a two-legged subject from one location to another by lifting and setting down each foot in turn. In another embodiment, walking is gait.

In another embodiment, the methods described herein are performed by altering posture/COP/COG by placing an anterior protuberance, a posterior protuberance or both. In another embodiment, the methods described herein involve wearing the device and performing daily activities with it, such as walking, household chores etc.

In another embodiment, the posterior protuberance, the anterior protuberance or both are placed in both the left and the right footwear to a position in which reduced posture imbalance is achieved. In another embodiment, altering posture/COP/COG with a protuberance comprises providing convexity, providing height, providing weight, providing position, providing base diameter, or any combination thereof of each protuberance for the sake of minimizing imbalance as described herein via alteration of faulty COP/COG/posture. In another embodiment, minimizing imbalance as described herein reduce pain of the subject. In another embodiment, minimizing imbalance as described herein described herein enhance the control over neuromuscular activity. In another embodiments, minimizing imbalance as described herein improves gait parameters of the subject.

In another embodiment, placement (being the function of the initial step of positioning a protuberance according to the invention) and calibration of a protuberance comprises disturbance, interruption, interposition, perturbation, obstruction, or any combination thereof of an imbalanced posture which results in reduction or correction of the imbalance.

In another embodiment, provided herein that the posterior protuberance is a bulbous protuberance. In another embodiment, provided herein that the anterior protuberance is a bulbous protuberance. In another embodiment, provided herein that both the posterior (P) protuberance and the anterior (A) protuberance are bulbous protuberances.

In some embodiments, the methods as described herein involve exercise with the device as described herein. In another embodiment, exercise is walking, running, dancing, jumping or any other form of gait movement. In another embodiment, treating is curing or improving the indication provided herein or symptoms related thereto. In some embodiments, treating is improving balance symmetry. In some embodiments, treating is reducing or completely eliminating pain felt by a subject. In some embodiments, treating is improving the overall posture/proprioception/kinesthesis parameters of a subject. In some embodiments, treating is improving posture/proprioception/kinesthesis. In some embodiments, treating is improving the stability of the subject. In some embodiments, treating is improving the velocity of the subject.

In some embodiments, treating is reducing muscle tone of the subject. In some embodiments, treating is increasing muscle tone of the subject. In some embodiments, treating is improving load distribution in the various joints of the subject. In some embodiments, treating is improving balance of the subject. In some embodiments, treating is Improving dysmetria of the subject. In some embodiments, treating is increasing neuronal sprouting (wherein neuronal sprouting is the process of growth in a damaged but still viable nerve cell (neuron), which can take place in the peripheral or central nervous systems) of the subject. In some embodiments, treating is increasing the impact of brain plasticity. In some embodiments, treating is preventing joint pain, deformity and contractures which are often the sequelae of neurological conditions. In some embodiments, treating is improving overall neuromuscular control of the subject. In another embodiment, treating is a process wherein the subject's disease or condition is ameliorated, or the symptoms related thereto are reduced or eliminated.

In another embodiment, the methods as described herein further comprises a combination treatment comprising the use of the device as described herein and a proper additional treatment that may include, for example, medication, surgery or any other medical and/or rehabilitation interventions. In another embodiment, one of skill in the art will readily diagnose and prescribe the proper medication, surgery or other medical and rehabilitation interventions to a subject suffering from a disease or a condition such as described herein.

In another embodiment, the outcome of treatment as provided herein is apparent immediately after the initial use of the device as described herein. In some embodiments, the outcome is apparent after initial calibration. In another embodiment, the outcome of treatment as provided herein is apparent after 10-1000000 meters of walking with the device as described herein. In another embodiment, the outcome of treatment as provided herein is apparent after 50-100000 meters of walking with the device as described herein. In another embodiment, the outcome of treatment as provided herein is apparent after 500-100000 meters of walking with the device as described herein. In another embodiment, the outcome of treatment as provided herein is apparent after 500-5000 meters of walking with the device as described herein. In another embodiment, the outcome of treatment as provided herein is apparent after 500-3000 meters of walking with the device as described herein.

In another embodiment, a device as disclosed herein has an immediate effect with regard to treating or treatment of a condition, disease, a pathology, and/or pain as provided herein. In another embodiment, short term immediate effect is apparent after walking with the device for 1-5 days. In another embodiment, short term immediate effect is apparent after walking with the device for 30-600 minutes. In another embodiment, short term immediate effect is apparent after walking with the device for 1-10 hours (hrs). In another embodiment, short term immediate effect is apparent after walking with the device for 5-1000 hours (hrs). In another embodiment, short term immediate effect is apparent after walking with the device for 12-96 hours (hrs). In another embodiment, short term immediate effect is apparent after walking with the device for 1-10 days. In another embodiment, short term immediate effect is apparent after walking with the device for 7-21 days. In another embodiment, short term immediate effect is apparent walking with the device for 5-30 days.

In another embodiment, the effect is apparent after walking with the device for 1-2 months. In another embodiment, the effect is apparent after walking with the device for 1-24 months. In another embodiment, the effect is apparent after walking with the device for 2-6 months. In another embodiment, the effect is apparent after walking with the device for 4-10 months. In another embodiment, the effect is apparent after walking with the device for 6-48 months. In another embodiment, the effect is apparent in after walking with the device for 12-24 months. In another embodiment, the effect is apparent after walking with the device for 10-30 months.

In another embodiment, any prescription as described herein comprises increase in daily usage time as the subject's imbalance improves. In another embodiment, any prescription as described herein comprises increase in daily usage time as subject's pain decreases. In another embodiment, any prescription as described herein comprises increase in daily usage time as subject's disease or condition as described herein, improves. In another embodiment, a prescription as described herein further comprises medicating or otherwise treating the subject according to his or hers medical condition.

In another embodiment, a prescription as described herein further comprises adjustments of the device as subject's posture/proprioception/kinesthesis is/are tuned or are off balance. In another embodiment, adjustments of the device comprise placing, providing or positioning a protuberance as described herein.

In another embodiment, the device is secured to a subject's foot directly. In another embodiment, the term "secured to a subject's foot" comprises securing the device to any footwear such as but not limited to shoes, boots, etc. that are secured to a subject's foot. In another embodiment, a foot securing means secures the device such as footwear as shown in the figures to a subject's foot. In another embodiment, various different foot securing means can be used. In another embodiment, a foot securing mean comprises a plurality of securing means. In another embodiment, a foot securing mean is a lace.

In another embodiment, the device is footwear comprising a shoe structure which includes at least two disturbances in the form of protuberances under the patient's feet. In another embodiment, the shoe structure serves as a platform for placing at least two calibrated, differential or identical disturbances or protuberances under the patient's feet according to the methods, system and computer program product, described herein.

In another embodiment, the upper part of the shoe structure serves as fastening or securing means/platform, while the sole is a platform for placing at least two calibrated, differential disturbances or protuberances under the patient's foot. In another embodiment, the outsole is a platform for placing at least two calibrated, differential or identical disturbances or protuberances under the patient's foot.

In another embodiment, a support member is operably attached to the securing mean. In another embodiment, operably attached comprises sufficient attachment between the securing mean and the support member. In another embodiment, a support member comprises the sole. In another embodiment, a support member comprises the inner sole. In another embodiment, a support member comprises the outer sole. In another embodiment, a support member comprises the middle sole. In another embodiment, a support member comprises the upper (the part of the shoe that is on top of the foot). In another embodiment, the upper is operably attached to the securing mean (such as but not limited to laces). In another embodiment, the upper comprises straps or totally enclosing the foot. In another embodiment, the upper comprises straps that function as securing means (such as sandals).

In another embodiment, a device such as footwear is supplied as one or more pairs of shoe-like devices, or alternatively, as just one of the shoe-like devices. In another embodiment, footwear comprises a support member having a periphery in a shape of a shoe sole comprising an upper surface.

In another embodiment, footwear is attached to a foot of a user by means of a boot 18 and/or fasteners, such as but not limited to, VELCRO straps, buckles, shoe laces, and the like. In another embodiment, footwear is attached to a foot of a user by means of a shoe. In another embodiment, a shoe comprises a platform of a sneaker. In another embodiment, the term sneaker comprises a boot. In another embodiment, the term sneaker comprises a walking boot. In another embodiment, a shoe comprises a platform of a running shoe. In another embodiment, a shoe comprises a platform of an elegant shoe. In another embodiment, a shoe comprises a platform of a walking shoe or boot.

In another embodiment, a device such as but not limited to boot is fashioned for attachment to the user's foot with or without fasteners. In another embodiment, fasteners 20 are used as foot securing means to attach footwear to the user's foot without boot.

In another embodiment, the invention provides that the device such as footwear comprises protuberances in a fixed position. In another embodiment, the invention provides that the device such as footwear comprises protuberances having any shape known to one of skill in the art which alters COP/COG in order to correct posture imbalance and perfect proprioception and/or kinesthesis. In another embodiment, the invention provides that the device comprises at least two bulbous protuberances. In another embodiment, a protuberance may be symmetrical. In another embodiment, a protuberance may be asymmetrical. In another embodiment, a protuberance comprises a shape of a: polygon, decagon, digon, dodecagon, nonagon, henagon hendecagon, heptagon, hexadecagon, hexagon icosagon, octagon, pentagon, triangle, Penrose tile, trapezium, isosceles, trapezium undecagon, quadrilateral, Lozenge, rhomboid, rectangle, square, rhombus, trapezoid, polydrafter, arbelos, circle, disc, circle, excircle, crescent, dome, ellipse, lune, oval, sphere, asteroid, or deltoid.

In another embodiment, each protuberance has a curved outer contour which alters COP/COG in order to correct posture imbalance and perfect proprioception and/or kinesthesis. In another embodiment, each protuberance has a different curved outer contour which alters COP/COG in order to correct posture imbalance and perfect proprioception and/or kinesthesis. In another embodiment, each protuberance has a convexity which alters COP/COG in order to correct posture imbalance and perfect proprioception and/or kinesthesis. In another embodiment, altering COP/COG in order to correct posture imbalance and perfect proprioception and/or kinesthesis is achieved by the methods, system and computer program product, described herein.

In another embodiment, a protuberance comprises a dome shape. In another embodiment, a protuberance as described herein comprises a dome shape which further comprises multiple different convexities. In another embodiment, each protuberance comprises a different convexity. In another embodiment, each protuberance comprises a different set of convexities.

In another embodiment, the contours may have the shape of a conic section, that is, the shape of a circle, ellipse, parabola or hyperbola. The various cross-sections of the contours of protuberance may be shaped identically or differently. In another embodiment, the shape of a protuberance is defined by equal arches. In another embodiment, the shape of a protuberance is defined by a variety of arches of different radiuses which are tangent to each other. In another embodiment, the shape of a protuberance is symmetrical. In another embodiment, the shape of a protuberance is asymmetrical. In another embodiment, a protuberance is a bulbous protuberance.

In another embodiment, the invention provides that the device such as footwear supports the foot of a subject only by the two protuberances when the two protuberances are placed on a ground surface. In another embodiment, the invention provides that the device such as footwear supports the foot of a subject during stance only by the two protuberances when the two protuberances are placed on a ground surface. In another embodiment, the invention provides that during stance only the 2 ground engaging surfaces of the protuberances (such as the peak or the surface facing the ground) are in contact with a ground surface. In another embodiment, the invention provides that during stance only the ground engaging surface in each protuberance is in contact with a ground surface.

In another embodiment, at least two bulbous protuberances protrude from a lower surface of support member. In another embodiment, only two bulbous protuberances protrude from a lower surface of support member. In another embodiment, a lower surface of support member is an outsole. In another embodiment, only two bulbous protuberances protrude from a lower surface of support member.

In another embodiment, the ground engaging parts of the device are only the protuberances. In another embodiment, during all phases of gait including the stance phase the protuberances are the only parts of the device which are ground engaging. In another embodiment, during all phases of gait including the stance phase the protuberances are the only parts of the device which are in direct contact with the ground.

In another embodiment, a protuberance as described herein is movable. In another embodiment, a protuberance as described herein is fixed. In another embodiment, a protuberance as described herein is 3D printed on an outsole in a position and shape which are determined according to the methods, system and computer program product, described herein. In another embodiment, a protuberance as described herein is replaceable. In another embodiment, a protuberance as described herein is movable along the outer surface or outsole of the support member. In another embodiment, a protuberance as described herein is movable along the outer surface of the outsole. In another embodiment, a protuberance as described herein can be positioned within the outer surface of the support member in a position determined according to the methods, system, and computer program product, described herein.

In another embodiment, a protuberance as described herein is movable or translatable such as in a track (e.g., forwards, backwards, sideways or diagonally) and/or rotatable about its own or other axis, or a combination of such motions.

In another embodiment, a protuberance has a base diameter of at least 35 mm. In another embodiment, a protuberance has a base diameter of at least 45 mm. In another embodiment, a protuberance has a base diameter of at least 55 mm. In another embodiment, a protuberance has a base diameter of at least 65 mm. In another embodiment, a protuberance has a base diameter of at least 75 mm. In another embodiment, a protuberance has a base diameter of at least 85 mm. In another embodiment, a protuberance has a base diameter of 35 to 95 mm. In another embodiment, a protuberance has a base diameter of 45 to 105 mm. In another embodiment, a protuberance has a base diameter of 45 to 95 mm. In another embodiment, a protuberance has a base diameter of 55 to 95 mm. In another embodiment, a wider base diameter is used to further stimulate weight bearing. In another embodiment, the flexibility in choosing different base diameters allows balancing a patient suffering from imbalance by stimulating differential weight bearing.

In another embodiment, a protuberance can be positioned anywhere on the support member. In another embodiment, a protuberance can be fixed anywhere on the support member. In another embodiment, a protuberance can be positioned and/or fixed anywhere within a predefined area. In another embodiment, the protuberance is hooked to a rail. In another embodiment, the protuberance is connected to a rail. In another embodiment, the protuberance is connected to a rail and is movable along the rail. In another embodiment, the protuberance is connected to a rail, is movable along the rail, and can be positioned and/or fixed anywhere along the rail.

In another embodiment, a protuberance is slidingly mounted on support member. In another embodiment, a protuberance is mounted on a track formed in the lower surface of support member and is selectively positioned anywhere along the track and fastened and or fixed thereto. In another embodiment, track extends along a portion of the shoe sole or all along the length of the shoe sole. Alternatively or additionally, the amount of protrusion of a protuberance is adjusted, such as by mounting protuberance with a threaded fastener to support member and tightening or releasing threaded fastener. In another embodiment, the term "fastening", "fixing" and "securing" are used interchangeably.

In another embodiment, a device as described herein further comprises an additional bulbous protuberance or bulbous protuberances, non-bulbous protuberance, or non-bulbous protuberances. In another embodiment, protuberances are formed in the shape of a peg, stud, bolt, pin, dowel and the like, although the invention is not limited to these shapes. In another embodiment, the protuberances' rigidity and/or flexibility is determined according to the methods, system and computer program product, described herein. In another embodiment, protuberances' resilience, elasticity, or hardness are determined according to the methods, system and computer program product, described herein. In another embodiment, protuberances protrude by different amounts from the lower surface of support member according to set values provided by the methods, system and computer program product, described herein. In another embodiment, the amount of protrusion of protuberances or height is set according to the methods, system and computer program product, described herein.

In another embodiment, the protuberances rise vertically and therefore each protuberance comprises a base end and a peak end. In another embodiment, the surface area of the base is larger than the surface area of the peak. In another embodiment, the peak is the ground engaging portion of a protuberance in the stance phase. In another embodiment, the peak is the ground engaging portion of a protuberance in all gait phases.

In another embodiment, positioning at least a first bulbous protuberance and a second bulbous protuberance in a position and shape which are determined according to the methods, system and computer program product, described herein.

In another embodiment, the bases of the protuberances are positioned on the centerline of the support member and the peaks of the protuberances are positioned on opposite sides of the centerline of support member. In another embodiment, the bases of the protuberances are positioned on the centerline of the support member, but the peaks of the protuberances are offset from the centerline of the support member. In another embodiment, the bases of the protuberances are positioned on the centerline of the support member, but the peaks of the protuberances are positioned on opposite sides of the centerline of the support member. In another embodiment, positioning a protuberance is positioning the peak or the ground engaging surface of a protuberance. In another embodiment, the terms "peak" and "ground engaging surface" are used interchangeably.

In another embodiment, the anterior protuberance is positioned medially from the centerline of the support member. In another embodiment, the peak of the anterior protuberance is positioned medially from the centerline of the support member. In another embodiment, the base of the anterior protuberance is positioned on the centerline of the support member, but the peak of the anterior protuberance is positioned medially from the centerline of the support member. In another embodiment, the anterior protuberance is positioned laterally from the centerline of the support member. In another embodiment, the peak of the anterior protuberance is positioned laterally from the centerline of the support member. In another embodiment, the base of the anterior protuberance is positioned on the centerline of the support member, but the peak of the anterior protuberance is positioned laterally from the centerline of the support member. In another embodiment, the posterior protuberance is positioned medially from the centerline of the support member. In another embodiment, the peak of the posterior protuberance is positioned medially from the centerline of the support member. In another embodiment, the base of the posterior protuberance is positioned on the centerline of the support member, but the peak of the posterior protuberance is positioned medially from the centerline of the support member. In another embodiment, the posterior protuberance is positioned laterally from the centerline of the support member. In another embodiment, the peak of the posterior protuberance is positioned laterally from the centerline of the support member. In another embodiment, the base of the posterior protuberance is position on the centerline of the support member, but the peak of the posterior protuberance is positioned laterally from the centerline of the support member.

The alignment of the protuberances is determined according to the methods, system and computer program product, described herein, for example, for tuning pelvic muscles.

In another embodiment, calibrating comprises positioning a protuberance on a support member. In another embodiment, calibrating comprises adjusting the height or protrusion of a protuberance. In another embodiment, calibrating comprises adjusting a resilience of a protuberance. In another embodiment, calibrating comprises adjusting a hardness of a protuberance. In another embodiment, calibrating comprises adjusting an elasticity of a protuberance. In another embodiment, calibrating instructions or calibration data are provided by the methods, system and computer program product, described herein.

In another embodiment, a protuberance is compressible. In another embodiment, a protuberance is deformable. In another embodiment, a protuberance is compressible or deformable upon pressure exerted by subject's weight.

In another embodiment, a protuberance is constructed of any suitable material, such as but not limited to, elastomers or metal or a combination of materials, and have different properties. In another embodiment, a protuberance comprises different resilience or hardness, such as having different elasticity properties or Shore hardness.

In another embodiment, a protuberance is a soft protuberance comprising a shore hardness of between 40 to 55 Sh A. In another embodiment, a protuberance is a medium hardness protuberance comprising a shore hardness of between 50 to 70 Sh A. In another embodiment, a protuberance is a hard protuberance comprising a shore hardness of between 65 to 90 Sh A.

In another embodiment, a protuberance has an abrasion between 1-60 mm$^3$ (by DIN 53516). In another embodiment, a protuberance comprises a rubber cup. In another embodiment, a protuberance comprises natural rubber compounds. In another embodiment, a protuberance comprises synthetic rubber compounds such as TPU, PU or TPR. In another embodiment, a protuberance comprises silicone. In another embodiment, a protuberance a plastic material such as PA 6 (nylon), PA6/6 (nylon)+glass fiber, ABS, Polypropylene, POM (Polyoxymethylene). In another embodiment, a protuberance comprises a metal such as aluminum, steel, stainless steel, brass, or metal alloys. In another embodiment, a protuberance comprises compound materials such as glass fibers, carbon fibers, aramid fibers (e.g., Kevlar®), or any combination thereof.

In another embodiment, different heights of a protuberance can be used. In another embodiment, a height of a protuberance is correlative or equal to the amount of protrusion and is determined by the methods, system and computer program as described herein. In another embodiment, the amount of protrusion is the distance from the surface of the support member to the ground engaging portion of a protuberance. In another embodiment, the amount of protrusion is the distance from the surface of the support member to the most distant ground engaging portion of a protuberance.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The invention claimed is:

1. A system comprising:

at least one hardware processor; and a non-transitory computer-readable storage medium having stored thereon program instructions, the program instructions executable by the at least one hardware processor to:

receive, with respect to one or more target subjects, sensor data from one or more of: inertial measurement units (IMUs), pressure sensors, and video capture systems, wherein the sensor data represents at least one of: center of pressure (COP), center of gravity (COG), and posture of a subject;

process the sensor data, by at least one of a sensor data engine and a computer vision engine, respectively, to extract a plurality of features comprising one or more of: gait velocity, step length, cadence, gait stance, gait swing, COP trajectory, COP velocity, pressure distribution, and lower extremity alignment; and apply a trained machine learning model to said features, to classify each of the one or more target subjects according to an abnormality, wherein the trained machine learning model comprises a Support Vector Machine (SVM) or a Deep Neural Network (DNN), wherein the trained machine learning model was trained using a training dataset comprising: (i) a plurality of features extracted from sensor data obtained from training subjects, wherein the sensor data comprises data from one or more of: inertial measurement units (IMUs), pressure sensors, and video capture systems; and (ii) annotation data representing analysis of abnormalities of the training subjects, wherein the annotation data comprises one or more of: abnormality type, abnormality severity, and abnormality degree of deviation, to classify abnormalities based on the features, wherein said abnormality comprises a biomechanical condition affecting at least one of: gait, posture, center of pressure (COP), and center of gravity (COG), wherein the system further comprises a decision module, configured to compute, based on said classification and said features, patient-specific perturbation positioning parameters for footwear, said parameters comprising at least a medial-lateral position and/or an anterior-posterior position and a height of a ground-engaging protuberance on an outsole, wherein application of said computed parameters is configured to alter the subject's center of pressure (COP) and/or center of gravity (COG) during gait to provide a training effect, and a 3D printer configured to print at least one protuberance on an outsole in a position and shape determined according to the computed parameters.

2. The system of claim 1, wherein training said machine learning model comprises:

receiving said plurality of features, obtained from a plurality of training subjects;

receiving annotation data representing analysis of one or more of: gait, posture, COP, COG, and proprioception of said training subjects; and training the machine learning model based on said plurality of features and said annotation data.

3. The system of claim 1, wherein said posture comprises one or more of dynamic posture and static posture.

4. The system of claim 1, wherein one or more of: said data element representing COP, said data element representing COG, and said data element representing posture, is received from one or more sensors selected from a list consisting: a weight sensor and a pressure sensor.

5. The system of claim 1, wherein said one or more data elements comprise a video segment depicting one or more of: gait, posture, and proprioception, of said subject.

6. The system of claim 1, wherein said plurality of features comprise one or more of: a gait velocity, a step length, cadence, plantar pressure distribution, gait stance, gait swing, single limb support, double limb support, gait symmetry, lower extremity range of motion, mean and max joint angle, coupling metrics, pressure distribution, COP trajectory, COP velocity, posture including upper extremity and lower extremity, lower extremity alignment, stride to stride variability, gait variability over time, gender, race, BMI, age, physical examination of joints, visual anatomy, foot alignment examination, and hyperlaxity.

7. The system of claim 1, wherein said information further comprises one or more clinical data elements selected from a list consisting of: history of different diseases and injuries, chronic ankle instabilities, history of ankle or other joint fractures, history of extremity fractures, history of overuse injuries, lower back pain, scoliosis, history of musculoskeletal disorders, comorbidities, regular pain medication intake, history of surgery in a lower extremity, and visual gait assessment parameters.

8. The system of claim 1, wherein said one or more clinical data elements further comprise one or more parameters reported by each of said subjects, said parameters are selected from a group consisting of: degree of pain experienced, degree of functional impairment experienced, and degree of quality-of-life impairment experienced.

9. The system of claim 2, wherein said analysis comprises one or more of: gait abnormality, gait abnormality severity, and gait abnormality source, posture abnormality, a proprioception disorder.

10. The system of claim 1, wherein said abnormality comprises one or more of: gait abnormality, gait abnormality severity, gait abnormality source, posture abnormality, posture abnormality severity, posture abnormality source and a proprioception disorder.

11. The system of claim 7, wherein said clinical data elements are received as one or more of: textual data, audio data, and visual data, wherein, said clinical data, is processed by said data processing engine, and wherein the data processing engine is a natural language processing algorithm.

12. A method comprising:

receiving, with respect to one or more target subjects, sensor data from one or more of: inertial measurement units (IMUs), pressure sensors, and video capture systems, wherein the sensor data represents at least one of: center of pressure (COP), center of gravity (COG), and posture of a subject;

processing the sensor data, by at least one of a sensor data engine and a computer vision engine, respectively, to extract a plurality of features comprising one or more of: gait velocity, step length, cadence, gait stance, gait swing, COP trajectory, COP velocity, pressure distribution, and lower extremity alignment;

applying a trained machine learning model to said features, to classify each of the one or more target subjects according to an abnormality, wherein the trained machine learning model comprises a Support Vector Machine (SVM) or a Deep Neural Network (DNN), wherein the trained machine learning model was trained using a training dataset comprising: (i) a plurality of features extracted from sensor data obtained from training subjects, wherein the sensor data comprises data from one or more of: inertial measurement units (IMUs), pressure sensors, and video capture systems; and (ii) annotation data representing analysis of abnormalities of the training subjects, wherein the annotation data comprises one or more of: abnormality type, abnormality severity, and abnormality degree of deviation, to classify abnormalities based on the features, wherein said abnormality comprises a biomechanical condition affecting at least one of: gait, posture, center of pressure (COP), and center of gravity (COG); and computing, by a decision module, based on said classification and said features, patient-specific perturbation positioning parameters for footwear, said parameters comprising at least a medial-lateral position and/or an anterior-posterior position and a height of a ground-engaging protuberance on an outsole, wherein application of said computed parameters is configured to alter the subject's center of pressure (COP) and/or center of gravity (COG) during gait to provide a training effect; and configuring the footwear by positioning at least one protuberance on an outsole according to the computed parameters.

13. The method according to claim 12 wherein training said machine learning model comprises:

receiving said plurality of features, obtained from a plurality of training subjects;

receiving annotation data representing analysis of one or more of: gait, posture, COP, COG, and proprioception of said training subjects; and training the machine learning model based on said plurality of features and said annotation data, to classify each of the one or more training subjects according to an abnormality.

14. The method of claim 13 wherein the annotated data is used as supervisory data in the training.

15. The method of claim 12, wherein said posture comprises one or more of: dynamic posture and static posture.

16. The method of claim 12, wherein said one or more data elements comprise a video segment depicting one or more of: gait, posture, and proprioception, of said subject.

17. The method of claim 12, wherein one or more of: said data element representing COP, said data element representing COG and said data element representing posture is received from one or more sensors selected from a list consisting: a weight sensor and a pressure sensor.

18. The method of claim 12, wherein said plurality of features comprises one or more of: a gait velocity, a step length, cadence, plantar pressure distribution, gait stance, gait swing, single limb support, double limb support, gait symmetry, lower extremity range of motion, mean and max joint angle, coupling metrics, pressure distribution, COP trajectory, COP velocity, posture including upper extremity and lower extremity, lower extremity alignment, stride to stride variability, and gait variability over time.

19. The method of claim 12, wherein said information further comprises a clinical data element, wherein said clinical data element comprises one or more of: gender, race, BMI, age, physical examination of joints, visual anatomy, foot alignment examination, hyperlaxity, history of different diseases and injuries, chronic ankle instabilities, history of ankle or other joint fractures, history of extremity fractures, history of overuse injuries, lower back pain, scoliosis, history of musculoskeletal disorders, comorbidities, regular pain medication intake, history of surgery in a lower extremity, visual gait assessment parameters, and one or more parameters reported by said subjects, said parameters are selected from the group consisting of: degree of pain experienced, degree of functional impairment experienced, and degree of quality-of-life impairment experienced.

20. The method of claim 12, wherein said abnormality comprises one or more of: gait abnormality, gait abnormality severity, gait abnormality source, posture abnormality, posture abnormality severity, posture abnormality source and a proprioception disorder.

* * * * *